(12) United States Patent
Vannucchi et al.

(10) Patent No.: US 9,993,480 B2
(45) Date of Patent: Jun. 12, 2018

(54) MTOR/JAK INHIBITOR COMBINATION THERAPY

(75) Inventors: Alessandro M. Vannucchi, Florence (IT); Costanza Bogani, Florence (IT); Paola Guglielmelli, Florence (IT)

(73) Assignees: NOVARTIS PHARMA AG, Basel (CH); INCYTE CORPORATION, Wilmington, DE (US)

( * ) Notice: Subject to any disclaimer, the term of this patent is extended or adjusted under 35 U.S.C. 154(b) by 462 days.

(21) Appl. No.: 13/399,274

(22) Filed: Feb. 17, 2012

(65) Prior Publication Data

US 2012/0214825 A1 Aug. 23, 2012

Related U.S. Application Data

(60) Provisional application No. 61/444,581, filed on Feb. 18, 2011, provisional application No. 61/503,789, filed on Jul. 1, 2011, provisional application No. 61/503,785, filed on Jul. 1, 2011.

(51) Int. Cl.
| C07D 487/04 | (2006.01) |
| A61K 31/519 | (2006.01) |
| A61K 31/436 | (2006.01) |
| A61K 45/06 | (2006.01) |

(52) U.S. Cl.
CPC ......... *A61K 31/519* (2013.01); *A61K 31/436* (2013.01); *A61K 45/06* (2013.01)

(58) Field of Classification Search
None
See application file for complete search history.

(56) References Cited

U.S. PATENT DOCUMENTS

| 5,521,184 | A  | 5/1996  | Zimmermann |
| 6,335,342 | B1 | 1/2002  | Longo et al. |
| 6,486,322 | B1 | 11/2002 | Longo et al. |
| 6,579,882 | B2 | 6/2003  | Stewart et al. |
| 6,635,762 | B1 | 10/2003 | Blumenkopf et al. |
| 6,852,727 | B2 | 2/2005  | Goulet et al. |
| 7,005,436 | B2 | 2/2006  | Lloyd et al. |
| 7,335,667 | B2 | 2/2008  | Rodgers et al. |
| 7,598,257 | B2 | 10/2009 | Rodgers et al. |
| 8,053,433 | B2 | 11/2011 | Rodgers et al. |
| 8,420,629 | B2 | 4/2013  | Rodgers et al. |
| 8,445,488 | B2 | 5/2013  | Rodgers et al. |
| 8,530,485 | B2 | 9/2013  | Rodgers et al. |
| 8,563,541 | B2 | 10/2013 | Arvanitis et al. |
| 8,604,043 | B2 | 12/2013 | Li et al. |
| 2003/0144309 | A1 | 7/2003  | Choon-Moon |
| 2003/0165576 | A1 | 9/2003  | Fujii et al. |
| 2004/0009983 | A1 | 1/2004  | Cox et al. |
| 2004/0029857 | A1 | 2/2004  | Hale et al. |
| 2004/0198737 | A1 | 10/2004 | Cox et al. |
| 2005/0153989 | A1 | 7/2005  | Grotzfeld et al. |
| 2006/0004010 | A1 | 1/2006  | Habashita et al. |
| 2006/0106020 | A1 | 5/2006  | Rodgers et al. |
| 2006/0183761 | A1 | 8/2006  | Ledeboer et al. |
| 2006/0183906 | A1 | 8/2006  | Rodgers et al. |
| 2007/0135461 | A1 | 6/2007  | Rodgers et al. |
| 2007/0135466 | A1 | 6/2007  | Ledeboer et al. |
| 2007/0149506 | A1 | 6/2007  | Arvanitis et al. |
| 2007/0208053 | A1 | 9/2007  | Arnold et al. |
| 2008/0188500 | A1 | 8/2008  | Arvanitis et al. |
| 2008/0207584 | A1 | 8/2008  | Habashita et al. |
| 2008/0312258 | A1 | 12/2008 | Rodgers et al. |
| 2008/0312259 | A1 | 12/2008 | Rodgers et al. |
| 2009/0018156 | A1 | 1/2009  | Tang et al. |
| 2009/0088445 | A1 | 4/2009  | Ledeboer et al. |
| 2009/0181959 | A1 | 7/2009  | Rodgers et al. |
| 2009/0197869 | A1 | 8/2009  | Arvanitis et al. |
| 2009/0215766 | A1 | 8/2009  | Rodgers et al. |
| 2009/0233903 | A1 | 9/2009  | Rodgers et al. |
| 2009/0318405 | A1 | 12/2009 | Li et al. |
| 2010/0113416 | A1 | 5/2010  | Friedman et al. |
| 2010/0190981 | A1 | 7/2010  | Zhou et al. |
| 2010/0209929 | A1* | 8/2010 | Fantl et al. ............... 435/6 |
| 2010/0298334 | A1 | 11/2010 | Rodgers et al. |
| 2011/0059951 | A1 | 3/2011  | Rodgers et al. |
| 2011/0086835 | A1 | 3/2011  | Rodgers et al. |
| 2011/0086810 | A1 | 4/2011  | Rodgers et al. |
| 2011/0082159 | A1 | 5/2011  | Rodgers et al. |
| 2011/0207754 | A1 | 8/2011  | Li et al. |
| 2011/0224157 | A1 | 9/2011  | Rodgers et al. |

(Continued)

FOREIGN PATENT DOCUMENTS

| DE | 30 36 390 | 5/1982 |
| WO | 97/02262 A1 | 1/1997 |

(Continued)

OTHER PUBLICATIONS

Ioannidis, S. et al., Medi 294, 240th National ACS meeting and Exposition, publication date Jul. 28, 2010.*
Scuto, A. et al, "The Novel JAK Inhibitor AZD1480 . . . ", Leukemia. Mar. 25, 2011(3): 558-550.*
FE Bertrand, Leukemia, 2005, 19, 98-102.*
Koopmans, S. M., et al., International Journal f Hematologic Oncology, Dec. 2013, vol. 2, No. 6, pp. 487-495.*
Daniela Cilloni MD PhD, Emanuela Messa MD, Antonia Rotolo MD & Giuseppe Saglio MD (2010) Emerging drugs for chronic myeloid leukemia, Expert Opinion on Emerging Drugs, 15:2, 175-184.*
Fiskus et al., Nov. 19, 2010; Blood: 116 (21).*
Mancini, et al., Journal of Cellular Biochemistry 109:320-328 (2010: )Published online Dec. 11, 2009.*
National Cancer Institute, http://www.cancer.gov/types/myeloproliferative/patient/chronic-treatment-pdq, Nov. 6, 2015.*
Kuwatsuka, et al., Blood Cancer J., May 1, 2011(5): e17.*
Tefferi, et al., Leukemia, 2008, 22, 14-22.*

(Continued)

*Primary Examiner* — Sreenivasan Padmanabhan
*Assistant Examiner* — Y Jeanmarie Z Calvillo
(74) *Attorney, Agent, or Firm* — Lathrop Gage LLP; Brian C. Trinque

(57) ABSTRACT

Provided herein is a combination therapy comprising an mTOR inhibitor and a JAK inhibitor. The combination therapy is useful for the treatment of a variety of cancers, including myeloproliferative neoplasms. The combination therapy is also useful for the treatment of any number of JAK-associated diseases.

23 Claims, 2 Drawing Sheets

(56) References Cited

U.S. PATENT DOCUMENTS

| | | |
|---|---|---|
| 2011/0224190 A1 | 9/2011 | Huang et al. |
| 2011/0263005 A1 | 10/2011 | Chang et al. |
| 2011/0288107 A1 | 11/2011 | Parikh et al. |
| 2012/0149681 A1 | 6/2012 | Rodgers et al. |
| 2012/0149682 A1 | 6/2012 | Rodgers et al. |
| 2012/0214825 A1 | 8/2012 | Vannucchi et al. |
| 2012/0301464 A1 | 11/2012 | Friedman et al. |
| 2013/0018034 A1 | 1/2013 | Yao et al. |
| 2013/0045963 A1 | 2/2013 | Rodgers et al. |
| 2013/0060026 A1 | 3/2013 | Zhou et al. |
| 2013/0137681 A1 | 5/2013 | Rodgers et al. |
| 2013/0225556 A1 | 8/2013 | Rodgers et al. |
| 2013/0253190 A1 | 9/2013 | Zhou et al. |
| 2013/0253191 A1 | 9/2013 | Zhou et al. |
| 2013/0253193 A1 | 9/2013 | Zhou et al. |

FOREIGN PATENT DOCUMENTS

| | | | |
|---|---|---|---|
| WO | 99/62908 A2 | 12/1999 | |
| WO | 99/65908 A1 | 12/1999 | |
| WO | 99/65909 A1 | 12/1999 | |
| WO | 2000/09495 A2 | 2/2000 | |
| WO | 2000/053595 A1 | 9/2000 | |
| WO | 01/014402 A1 | 3/2001 | |
| WO | 01/42246 A2 | 6/2001 | |
| WO | 01/064655 A1 | 9/2001 | |
| WO | 01/81345 A1 | 11/2001 | |
| WO | 02/000196 A2 | 1/2002 | |
| WO | 02/00661 A1 | 1/2002 | |
| WO | 02/055084 A1 | 7/2002 | |
| WO | 02/060492 A1 | 8/2002 | |
| WO | 02/096909 A1 | 12/2002 | |
| WO | 03/011285 A1 | 2/2003 | |
| WO | 03/024967 A2 | 3/2003 | |
| WO | 03/037347 A1 | 5/2003 | |
| WO | 03/048162 A1 | 6/2003 | |
| WO | 03/099771 A2 | 12/2003 | |
| WO | 04/005281 A1 | 1/2004 | |
| WO | 04/041814 A1 | 5/2004 | |
| WO | 04/046120 A2 | 6/2004 | |
| WO | 04/047843 A1 | 6/2004 | |
| WO | 04/056786 A2 | 7/2004 | |
| WO | 04/072063 A1 | 8/2004 | |
| WO | 04/080980 A1 | 9/2004 | |
| WO | 04/099204 A1 | 11/2004 | |
| WO | 04/099205 A1 | 11/2004 | |
| WO | 05/013986 A1 | 2/2005 | |
| WO | 05/028444 A1 | 3/2005 | |
| WO | 05/051393 A1 | 6/2005 | |
| WO | 05/060972 A2 | 7/2005 | |
| WO | 05/095400 A1 | 10/2005 | |
| WO | 05/105146 A1 | 11/2005 | |
| WO | 05/105814 A1 | 11/2005 | |
| WO | 05/105988 A2 | 11/2005 | |
| WO | 05/110410 A2 | 11/2005 | |
| WO | 05/121130 A2 | 12/2005 | |
| WO | 06/013114 A1 | 2/2006 | |
| WO | 06/046023 A1 | 5/2006 | |
| WO | 06/046024 A1 | 5/2006 | |
| WO | 06/056399 A2 | 6/2006 | |
| WO | 06/069080 A2 | 6/2006 | |
| WO | 06/096270 A1 | 9/2006 | |
| WO | 06/122806 A2 | 11/2006 | |
| WO | 06/127587 A1 | 11/2006 | |
| WO | 06/129199 A2 | 12/2006 | |
| WO | 06/136823 A1 | 12/2006 | |
| WO | 07/002433 A1 | 1/2007 | |
| WO | 07/025090 A2 | 3/2007 | |
| WO | 07/041130 A2 | 4/2007 | |
| WO | 2007/047754 A2 | 4/2007 | |
| WO | 07/062459 A1 | 6/2007 | |
| WO | 07/070514 A1 | 6/2007 | |
| WO | 07/076423 A2 | 7/2007 | |
| WO | 07/077949 A1 | 7/2007 | |
| WO | 07/084557 A2 | 7/2007 | |
| WO | 07/117494 A1 | 10/2007 | |
| WO | 08/145688 A2 | 12/2008 | |
| WO | 08/157208 A2 | 12/2008 | |
| WO | 09/049028 A1 | 4/2009 | |
| WO | 09/064835 A1 | 5/2009 | |
| WO | 2009/097309 A1 | 8/2009 | |
| WO | 09/114512 A1 | 9/2009 | |
| WO | WO 2009137378 A2 * | 11/2009 | |
| WO | 2010/062571 A1 | 6/2010 | |
| WO | 10/081692 A1 | 7/2010 | |
| WO | WO 2012033537 * | 3/2012 | ............ C40B 30/06 |
| WO | WO 2012/112847 A1 | 8/2012 | |
| WO | 13/023119 A1 | 2/2013 | |

OTHER PUBLICATIONS

Anderson et al: Biochemical characterization of GSK1070916, a potent and selective inhibitor of Aurora B and Aurora C kinases with an extremely long residence time; Biochem J; vol. 420, pp. 259-265 (2009).

Baudouin: Flow Cytometry in Impression Cytology Specimens; Investigative Ophthalmology & Visual Science; vol. 38(7), pp. 1458-1464 (1997).

Bollrath et al: gp130-Mediated Stat3 Activation in Enterocytes Regulates Cell Survival and Cell-Cycle Progression during Colitis-Associated Tumorigenesis; Cancer Cell, vol. 15:91-102 (2009).

Bromberg et al: Inflammation and Cancer: IL-6 and STAT3 Complete the Link; Cancer Cell, vol. 15 (2), pp. 79-80 (2009).

Carey, Francis A. et al: Oxidations; Advanced Organic Chemistry; Fourth Edition, Kluwer Academic/Plenum Publishers, New York, Chpt. 12, pp. 747-757 (2001).

Gaertner, Van R., "Cyclization of 1-Alkylamino-3-halo-2-alkanols to 1-Alkyl-3-azetidinols," J. Org. Chem., vol. 32 (10):2972-2976 (1967).

Gooseman, Natalie E.J. et al., "The intramolecular beta-fluorine-ammonium interaction in 4- and 8-membered rings," Chem. Commun., vol. 30:3190-3192 (2006).

Hamze, Abdallah et al., "Synthesis of Various 3-Substituted 1,2,4-Oxadiazole-Containing Chiral b3- and a-Amino Acids from Fmoc-Protected Aspartic Acid," J. Org. Chem., vol. 68:7316-7321 (2003).

Hardwicke, Mary Ann et al., "GSK1070916, a potent Aurora B/C kinase inhibitor with broad antitumor activity in tissue culture cells and human tumor xenograft models," Mol. Cancer Ther., vol. 8(7):1808-1817 (2009).

Helal, Christopher J. et al., "Stereoselective Synthesis of cis-1,3-Disubstituted Cyclobutyl Kinase Inhibitors," Organic Letters, vol. 6(11):1853-1856 (2004).

Higuchi, T. et al., Pro-drugs as Novel Drug Delivery Systems, ACS Symposium Series: American Chemical Society, Washington, D.C., vol. 14 (1974), 240 pages.

International Preliminary Report on Patentability for Application No. PCT/US2008/066662, dated Dec. 17, 2009, 16 pages.

Lin, et al.; Enantioselective Synthesis of Janus Kinase Inhibitor INCB018424 via an Organocatalytic Aza-Michael Reaction; American Chemical Society, Org. Lett., vol. 11, No. 9, 2009, pp. 1999-2002.

Sawada, et al.; Increased Lipophilicity and Subsequent Cell Partitioning Decrease Passive Transcellular Diffusion of Novel, Highly Lipophilic Antioxidants; J Pharmacology and Experimental Therapeutics; 1999; vol. 288, No. 3, pp. 1317-1326.

Abstract of Chilean patent application No. 3496-06, published in Official Gazette of the Republic of Chile, Jun. 1, 2007, 1 page.

Letter from Chilean foreign counsel reporting the publication of the abstract of Chilean patent application No. 3496-06, Jun. 5, 2007, 1 page.

Schindler, et al.; Cytokines and STAT Signaling; Advances in Pharmacology: Hormones and Signaling; 2000;47:113-74.

Roudebush, Roger E.; Pharmacologic manipulation of a four day murine delayed type hypersensitivity model; Agents Actions.; Jan. 1993; 38(1-2):116-21.

26th Annual JPMorgan Healthcare Conference presentation dated Jan. 8, 2008, 28 pages.

(56) References Cited

OTHER PUBLICATIONS

Bell, Malcolm, and Zalay, Andrew, "Synthesis of Substituted 3-Amino[6, 5-b] triazmmdoles." Journal of Heterocyclic Chemistry, 12(5):1001-1004, Oct. 1975.

Gorr, M.E. et al., "Clinical Resistance to STI-571 Cancer Therapy Caused by BCR-ABL Gene Mutation or Amplification." Science, 293:876, 2001.

Blume-Jensen et al: Oncogenic kinase signalling; Nature; 2001, vol. 411, pp. 355-365.

Bolen: Nonreceptor tyrosine protein kinases; Oncogene; 1993, vol. 8(8), pp. 2025-2031.

Borie et al: Combined Use of the JAK3 Inhibitor CP-690,550 with Mycophenolate Mofetil to Prevent Kidney Allograft Rejection in Nonhuman Primates; Transplantation; 2005, vol. 80, No. 12, pp. 1756-1764.

Boudny et al: JAK/STAT signaling pathways and cancer; J Neoplasm; 2002, vol. 49, pp. 349-355.

Bowman et al: STATs in oncogenesis; Oncogene, 2000, vol. 19, pp. 2474-2488.

Burger et al: Gp130 and ras mediated signaling in human plasma cell line INA-6: a cytokine-regulated tumor model for plasmacytoma; Hematol J; 2001, vol. 2, pp. 42-53.

Candotti et al: Molecular aspects of primary immunodeficiencies: lessons from cytokine and other signaling pathways; J Clin Invest; 2002, vol. 109(10), pp. 1261-1269.

Candotti et al: Structural and functional basis for JAK3-deficient severe combined immunodeficiency; Blood; 1997, vol. 90(10): 3996-4003.

Cetkovic-Cvrlje et al: Targeting JAK3 with JANEX-1 for prevention of autoimmune type 1 diabetes in NOD mice; Clin Immunol; 2003, vol. 106(3): 213-25.

Chalandon et al: Targeting mutated protein tyrosine kinases and their signaling pathways in hematologic malignancies; Hematologica; 2005, vol. 90, pp. 949-968.

Changelian et al: Prevention of Organ Allograft Rejection by a Specific Janus Kinase 3 Inhibitor; Science; 2003, vol. 302, pp. 875-878.

Chen et al: Stat3 Activation in Human Endometrial and Cervical Cancer; British Journal of Cancer, 2007, vol. 96, pp. 591-599.

Conklyn, M. et al: The JAK3 inhibitor CP-690550 Selectively reduces NK and CD8+ cell numbers cynomolgus monkey blood following chronic oral dosing; Journal of Leukocyte Biology, 2004, vol. 76, pp. 1248-1255.

Gotlieb, Alice, Presentation at the 2008 American Academy of Dermatology, 66th Annual Meeting, San Antonio, TX, Feb. 1, 2008, Symposium-303, 12 pages.

Daniels et al., "Imatinib mesylate inhibits the profibrogenic activity of TGF-13 and prevents bleomycinmediated lung fibrosis." J. Clin. Invest., 114(9):1308-1316, Nov. 2004.

Deuse et al: Novel Immunosuppression: R348, a JAK3- and Syk-Inhibitor Attenuates Acute Cardiac Allograft Rejection; Transplantation; 2008, vol. 85(6), pp. 885-892.

Doleschall G., and Lempert, K., "Thermal and Acid Catalysed Degradations of 3-Alkylthio-6,7-Dihydro-[1.2.4] Triazino[1.6-C]Quinazolin-5-Ium-I-Olates." Tetrahedron, 30:3997-4012, 1974.

De Vos, J., M. Jourdan, et al., "JAK2 tyrosine kinase inhibitor tyrphostin AG490 downregulates the mitogen-activated protein kinase (MAPK) and signal transducer and activator of transcription (STAT) pathways and induces apoptosis in myeloma cells." Br J Haematol, 2000, vol. 109(4): 823-8.

Dudley et al: A VEGF/JAK2/STAT5 axis may partially mediate endothelial cell tolerance to hypoxia; Biochem. J.; 2005, vol. 390, pp. 427-436.

Quesada et al: One-pot conversion of activated alcohols into 1,1-dibromoalkenes and terminal alkynes using tandem oxidation processes with manganese dioxide; Tetrahedron; 2006, vol. 62, pp. 6673-6680.

Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007, 1 page.

Fridman, Jordan, et al. "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov. 8-10, 2007. Poster 0009, 1 page.

Fridman, Jordan et al. "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, Poster 285, 1 page.

Fridman, Jordan et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007, 1 page.

Fridman, J. et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark, 1 page.

Fiskus et al: Synergistic Activity of Combinations of JAK2 Kinase Inhibitor with PI3K/mTOR, MEK OR PIM Kinase Inhibitor Against Human Myeloproliferative Neoplasm Cells Expressing JAK2V617F; J. Amer Chem Soc; 52nd Annual Meeting of the American-Society of Hematology; Orlando, FL, USA; Dec. 4-7, 2010, Abstract, ACS Publications, US, 1 page.

APExBIO "Ruxolitinib (INCB018424)JAK inhibitor," Accssible on the INternet at URL: http://www.apexbt.com/ruxolitnib.html. [Last Accessed Mar. 14, 2016].

Fiskus et al. (2010) "Synergistic activity of combinations of JAK2 kinase inhibitor with PI3K/mTOR, MEK or kinase inhibitor against human myeloproliferative neoplasm cells expressing JAK2V617F," In; Oral and Poster Abstracts of the 53rd Annual Meeting of the Society of Hematology. Abstract 798.

Guglielmelli et al. (Jul. 2011) "Safety and efficacy of everolimus, a mTOR inhibitor, as single agent in a phase 1/2 study in patients with myelofibrosis," Blood J. 188(8):2069-2076.

Leibniz-Institute "Cell Line: BA/F3," DSMZ No. ACC 300. Accessible on the Internet at URL: https://www.dsmz.de/catalogues/details/culture/ACC-300.html. [Last Accessed Mar. 14, 2016].

Leibniz-Institute "Cell Line: SET-2," DSMZ No. ACC 608. Accessible on the Internet at URL: https://www.dsmz.de/catalogues/details/culture/ACC-608.html. [Last Accessed Mar. 8, 2016].

Liu et al. (2009) "mTOR Mediated Anti-Cancer Drug Discovery," Drug Discovery Today: Therapeutic Strategies. 6 (2):47-55.

Loh (Mar. 2011) "Recent advances in the pathogenesis and treatment of juvenile myelomonocytic leukaemia," Br. J. Haematol. 152(6):677-687.

McLornan (2006) "JAK2 V617F: a single mutation in the myeloproliferative group of disorders," Ulster Medical Journal. 75(2):112-119.

Tefferi et al. (2008) "Essential thrombocythemia, polycythemia vera, and myelofibrosis: Current management and the prospect of targeted therapy," Am. J. Hematol. 83:491-497.

Vannucchi et al. (2010) "A Phase 1/2 Study of RAD001, a mTOR Inhibitor, In Patients with Myelofibrosis: Final Results," In; Oral and Poster Abstracts of the 53rd Annual Meeting of the Society of Hematology. Abstract 314.

Vannucchi (Dec. 12, 2011) "Inhibitors of PI3K/Akt and/or mTOR Inhibit the Growth of Cells of Myeloproliferative Neoplasms and Synergize with JAK2 Inhibitor and Interferonm," In; Oral and Poster Abstracts of the 53rd Annual Meeting of the Society of Hematology. Abstract 3835.

Verstovsek et al. (2007) INCB018424, an oral, selective JAK2 inhibitor, shows significant clinical activity in a phase I/II study in patients with primary myelofibrosis (PMF) and post polycythemia vera/essential thrombocythemia myelofibrosis (post-PV/ET MF) Blood J. 110(11):558.

Third Party Opposition to European Patent No. 2 675 451, dated Mar. 24, 2016.

(56) References Cited

OTHER PUBLICATIONS

U.S. Appl. No. 12/137,883 (U.S. Pat. No. 7,834,022), filed Jun. 12, 2008 (Issued Nov. 16, 2010), James D. Rodgers.
U.S. Appl. No. 12/137,892, filed Jun. 12, 2008, James D. Rodgers.
U.S. Appl. No. 14/097,588, filed Dec. 5, 2013, James D. Rodgers.
U.S. Appl. No. 14/097,598, filed Dec. 5, 2013, James D. Rodgers.
U.S. Appl. No. 12/687,623 (U.S. Pat. No. 8,410,265), filed Jan. 14, 2010 (Issued Apr. 2, 2013), Jiacheng Zhou.
U.S. Appl. No. 13/761,742, filed Feb. 7, 2013, Jiacheng Zhou.
U.S. Appl. No. 13/761,771, filed Feb. 7, 2013, Jiacheng Zhou.
U.S. Appl. No. 13/761,830, filed Feb. 7, 2013, Jiacheng Zhou.
U.S. Appl. No. 12/901,001 (U.S. Pat. No. 8,486,902), filed Oct. 8, 2010 (Issued Jul. 16, 2013), James D. Rodgers.
U.S. Appl. No. 13/917,124, filed Jun. 13, 2013, James D. Rodgers.
U.S. Appl. No. 13/030,682, filed Feb. 18, 2011, Yun-Long Li.
U.S. Appl. No. 13/399,274, filed Feb. 17, 2012, Alessandro M. Vannucchi.
U.S. Appl. No. 13/571,525, filed Aug. 10, 2012, Alessandro M. Vannucchi.
U.S. Appl. No. 11/115,702, filed Apr. 27, 2005, James D. Rodgers.
U.S. Appl. No. 11/313,394 (U.S. Pat. No. 7,335,667), filed Dec. 21, 2005 (Issued Feb. 26, 2008), James D. Rodgers.
U.S. Appl. No. 11/524,641, filed Sep. 21, 2006, Argyrios G. Arvanitis.
U.S. Appl. No. 11/637,545 (U.S. Pat. No. 7,598,257), filed Dec. 12, 2006 (Issued Oct. 6, 2009), James D. Rodgers.
U.S. Appl. No. 11/961,424 (U.S. Pat. No. 8,513,270), filed Dec. 20, 2007 (Issued Aug. 20, 2013), Argyrios G. Arvanitis.
U.S. Appl. No. 11/980,314 (U.S. Pat. No. 8,053,433), filed Oct. 30, 2007 (Issued Nov. 8, 2011), James D. Rodgers.
U.S. Pat. No. 12/138,082 (U.S. Pat. No. 8,415,362), filed Jun. 12, 2008 (Issued Apr. 9, 2013), James D. Rodgers.
U.S. Appl. No. 12/187,061, filed Aug. 6, 2008, James D. Rodgers.
U.S. Appl. No. 12/270,135 (U.S. Pat. No. 8,309,718), filed Nov. 13, 2008 (Issued Nov. 13, 2012), Yun-Long Li.
U.S. Appl. No. 12/401,348 (U.S. Pat. No. 8,158,616), filed Mar. 10, 2009 (Issued Apr. 17, 2012), James D. Rodgers.
U.S. Appl. No. 12/418,132, filed Apr. 3, 2009, Argyrios G. Arvanitis.
U.S. Appl. No. 12/571,834, filed Oct. 1, 2009, Paul A. Friedman.
U.S. Appl. No. 12/784,916, filed May 21, 2010, James D. Rodgers.
U.S. Appl. No. 12/785,057 (U.S. Pat. No. 8,604,043), filed May 21, 2010 (Issued Dec. 10, 2013), Yun-Long Li.
U.S. Appl. No. 12/872,925, filed Aug. 31, 2010, James D. Rodgers.
U.S. Appl. No. 13/043,986, filed Mar. 9, 2011, Taisheng Huang.
U.S. Appl. No. 13/076,176 (U.S. Pat. No. 8,530,485), filed Mar. 30, 2011 (Sep. 10, 2013), James D. Rodgers.
U.S. Appl. No. 13/076,220, filed Mar. 30, 2011, James D. Rodgers.
U.S. Appl. No. 13/112,370, filed May 20, 2011, Bhavnish Parikh.
U.S. Appl. No. 13/245,333 (U.S. Pat. No. 8,445,488), filed Sep. 26, 2011 (Issued May 21, 2013), James D. Rodgers.
U.S. Appl. No. 13/300,094, filed Nov. 18, 2011, James D. Rodgers.
U.S. Appl. No. 13/300,137, filed Nov. 18, 2011, James D. Rodgers.
U.S. Appl. No. 13/315,750 (U.S. Pat. No. 8,420,629), filed Dec. 9, 2011 (Issued Apr. 16, 2013), James D. Rodgers.
U.S. Appl. No. 13/479,045 (U.S. Pat. No. 8,563,541), filed May 23, 2012 (Issued Oct. 22, 2013), Argyrios G. Arvanitis.
U.S. Appl. No. 13/526,957, filed Jun. 19, 2012, Wenqing Yao.
U.S. Appl. No. 13/588,776, filed Aug. 17, 2012, James D. Rodgers.
U.S. Appl. No. 13/564,271, filed Aug. 1, 2012, Paul A. Friedman.
U.S. Appl. No. 13/605,331, filed Sep. 6, 2012, Jiacheng Zhou.
U.S. Appl. No. 13/754,533, filed Jan. 30, 2013, James D. Rodgers.
U.S. Appl. No. 13/853,475, filed Mar. 29, 2013, James D. Rodgers.
Grabbe, et al: Immunoregulatory mechanisms involved in elicitation of allergic contact hypersensitivity; Immunol Today; 1998, vol. 19(1), pp. 37-44.
Ishizaki et al: Pharmacological Properties of Y-27632, a Specific Inhibitor of Rho-Associated Kinases; Molecular Pharmacology; 2000, vol. 57, pp. 976-983.
Itagaki et al: Expedient Synthesis of Potent Cannabinoid Receptor Agonist (−)-CP55,940; Organic Letters; 2005, vol. 7(19), pp. 4181-4183.
James et al: A unique clonal JAK2 mutation leading to constitutive signalling causes polycythaemia vera; Nature; 2005, vol. 434, pp. 1144-1148.
Zou et al: Signaling Pathways Activated by Oncogenic Forms of Abl Tyrosine Kinase; Journal of Biological Chemistry; 1999, vol. 274(26), pp. 18141-18144.
Kawamura et al: Molecular cloning of L-JAK, a Janus family protein-tyrosine kinase expressed in natural killer cells and activated leukocytes; Proc Natl Acad Sci USA, 1994, vol. 91(14), pp. 6374-6378.
Kharas et al: ABL Oncogenes and Phosphoinositide 3-Kinase: Mechanism of Activation and Downstream Effectors; Cancer Res; 2005, vol. 65(6), pp. 2047-2053.
Kruh et al: The complete coding sequence of arg defines the Abelson subfamily of cytoplasmic tyrosine kinases; Proc. Natl. Acad. Sci., 1990, vol. 87, pp. 5802-5806.
Kubinyi: Qsar: Hansch Analysis and Related Approaches; Methods and Principles in Medicinal Chemistry; eds, Manhold et al., Weinhein, NY, 1993, 42 pages.
Kudelacz et al: The JAK-3 inhibitor CP-690550 is a potent anti-inflammatory agent in a murine model of pulmonary eosinophilia; European Journal of Pharmacology; 2008, vol. 582, pp. 154-161.
Levine, et al: Activating mutation in the tyrosine kinase JAK2 in polycythemia vera, essential thrombocythemia, and myeloid metaplasia with myelofibrosis; Cancer Cell, 2005, vol. 7, pp. 387-397.
Madhusudan: Tyrosine kinase inhibitors in cancer therapy; Clin Biochem; 2004, vol. 37(7), pp. 618-635.
Manning et al: The Protein Kinase Complement of the Human Genome; Science; 2002, vol. 298, pp. 1912-1934.
Wu et al: One-Pot Two-Step Microwave-Assisted Reaction in Constructing 4,5-disubstituted Pyrazolopyrimidines; Organic Letters, 2003, vol. 5(20), pp. 3587-3590.
Milici, A.J., et al: Cartilage preservation by inhibition of Janus kinase 3 in two rodent models of rheumatoic arthritis; Arthritis Research & Therapy 2008, 10:R14 (http://arthritis-research.com/content/10/1/R14), 9 pages.
Nakagawara, Akira, "Trk receptor tyrosine kinases: A bridge between cancer and neural development." Cancer Letters, 2001, vol. 169, pp. 107-114.
Neubauer et al: JAK2 Deficiency Defines an Essential Developmental Checkpoint in Definitive Hematopoiesis; Cell; 1998, vol. 93(3), pp. 397-409.
Nishio et al: Tyrosine kinase-dependent modulation by interferon-alpha of the ATP-sensitive K+ current in rabbit ventricular myocytes; FEBS Letters; 1999, vol. 445, pp. 87-91.
Palmer, Amparo, and Klein, Rudiger, "Multiple roles of ephrins in morphogenesis, neuronal networking, and brain function." Genes & Dev., 17:1429-1450, 2003.
Patani, G.A. et al: Bioisosterism: A Rational Approach in Drug Design; Chem. Rev. 1996, vol. 96, pp. 3147-3176.
Parganas et al: Jak2 Is Essential for Signaling through a Variety of Cytokine Receptors; Cell; 1998, vol. 93(3), pp. 385-395.
Park et al: Homogeneous Proximity Tyrosine Kinase Assays: Scintillation Proximity Assay versus Homogeneous Time-Resolved Fluorescence; Analytical Biochemistry; 1999, vol. 269, pp. 94-104.
Pernis et al: JAK-STAT signaling in asthma; J Clin Invest; 2002, vol. 109(10), pp. 1279-1283.
International Search Report and Written Opinion for PCT/US2006/047369, dated Apr. 24, 2007, 16 pages.
Press Release dated Sep. 18, 2008: Incyte's Topical JAK Inhibitor Demonstrates Positive Proof-of-Concept Results in Patients with Mild to Moderate Psoriasis, 4 pages.
Punwani, et al. "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008, poster presentation, 15 pages.
Remington's Pharmaceutical Sciences, 17th ed., Mack Publishing Company, Easton, Pa., 1985, p. 1418.

(56) References Cited

OTHER PUBLICATIONS

Rodig et al: "Disruption of the Jak1 gene demonstrates obligatory and nonredundant roles of the Jaks in cytokine-induced biologic responses." Cell, 1998, vol. 93(3), pp. 373-383.
Rousvoal et al: Janus kinase 3 inhibition with CP-690,550 prevents allograft vasculopathy; Transpl Int; 2006,vol. 12, pp. 1014-1021.
Saemann, M. D., C. Diakos, et al. (2003). "Prevention of CD40-triggered dendritic cell maturation and induction of T-cell hyporeactivity by targeting of Janus kinase 3." Am J Transplant, vol. 3(11), pp. 1341-1349.
Scott, M. J., C. J. Godshall, et al. (2002). "Jaks, STATs, Cytokines, and Sepsis." Clin Diagn Lab Immunol 9(6): 1153-9.
Seto, Y., H. Nakajima, et al. (2003). "Enhanced Th2 cell-mediated allergic inflammation in Tyk2-deficient mice." J Immunol 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.
Sriram et al: Induction of gp130-related Cytokines and Activation of JAK2/STAT3 Pathway in Astrocytes Precedes Up-regulation of Glial Fibrillary Acidic Protein in the 1-Methyl-4phenyl1-1,2,3,6-tetrahydropyridine Model of neurodegeneration; J. Biol. Chem; 2004, vol. 279(19), pp. 19936-19947.
Staerk et al: JAK1 and Tyk2 Activation by the Homologous Polycythemia Vera JAK2 V617F Mutation, Cross-Talk With IGF1 Receptor; JBC; 2005, vol. 280, pp. 41893-41899.
Tefferi, A. et al.; The Clinical Phenotype of Myelofibrosis Encompasses a Chronic Inflammatory State that is Favorably Altered by INCB018424, A Selective Inhibitor of JAK1/2; Poster #2804 at The American Society of Hematology Annual Meeting (ASH), Dec. 7, 2008, 2 pages.
Ortmann, R. A., T. Cheng, et al. Janus kinases and signal transducers and activators of transcription: their roles in cytokine signaling, development and immunoregulation; Arthritis Res; 2000, vol. 2(1), pp. 16-32.
Takemoto, S., J. C. Mulloy, et al. (1997). "Proliferation of adult T cell leukemia/lymphoma cells is associated with the constitutive activation of JAK/STAT proteins." Proc Natl Acad Sci U S A 94(25): 13897-902.
Thompson et al: Photochemical Preparation of a Pyridone Containing Tetracycle: a Jak Protein Kinase Inhibitor; Bioorganic & Medicinal Chemistry Letters, vol. 12 (2002), pp. 1219-1223.
Verstovsek, S., et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007.
Verstovsek, S., et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET ME)" Abstract #0444, presented Saturday, Jun. 14, 2008 at the European Hematology Association, 13th Congress, Jun. 12-15, Copenhagen, Denmark; 2 pages.
Verstovsek, S. et al.; INCB18424 Discussion, American Society of Hematology, Dec. 10, 2007; presentation, 16 pages.
Verstovsek, S., et al.; Characterization of JAK2 V617F Allele Burden in Advanced Myelofibrosis (MF) Patients: No Change in V617F:WT JAK2 Ratio in Patients with High Allele Burdens Despite Profound Clinical Improvement Following Treatment with the JAK Inhibitor INCB018242, Poster #2802 at the American Society of Hematoloogy Annual Meeting (ASH), Dec. 7, 2008, 2 pages.
Verstovsek, S. et al.; The JAK Inhibitor, INCB018242, Demonstrates Durable and Marked Clinical Responses in Primary Myelofibrosis (PMF) and Post-Polycythemia/Essential Thrombocythemia Myelofibrosis (Post PV/ET-MF), Poster #1762, 2 pages.
Verbeeck, et al.; Biowaiver Monographs for Immediate Release Solid Oral Dosage Forms Based on Biopharmaceutics Classification System (BCS) Literature Data: Chloroquine Phosphate, Chloroquine Sulfate, and Chloroquine Hydrochloride; J Pharma Sci; 2005, 94:7, 1389-1395.
Seefeld, et al., Discovery of 5-pyrrolopyridinyl-2-thiophenecarboxamides as potent AKT kinase inhibitors; Bioorganic & Medicinal Chemistry Letters 19 20092244-2248.
Chloroquine phosphate, material data safety sheet 9MSDS), downloaded Jun. 15, 2010 <http://www.sciencelab.com/xMSDS-Chloroquine_phosphate-9923444>; pp. 1-6.
Chloroquine phosphate, material data safety sheet 9MSDS), downloaded Jun. 15, 2010 <http://www.lookchem.com/Chloroquine/>; pp. 1-6.
Berge et al: Pharmaceutical Salts; J. of Pharmaceutical Sciences; 1977, vol. 66(1), pp. 1-19.
International Search Report and Written Opinion, PCT/US2012/050252, dated Jan. 2, 2013, 11 pages.
International Search Report and Written Opinion, PCT/US2012/025581, dated 26 Apr. 26, 2012, 16 pages.
Janes et al: Effective and selective targeting of leukemia cells using a TORC1/2 kinase inhibitor; Nature Medicine; 2010, vol. 16, No. 2, pp. 205-213.
Mancini et al: RAD001 (everolimus) prevents mTOR and Akt late re-activation in response to imatinib in chronic myeloid leukemia; J Cellular Biochemistry; 2010, vol. 109, No. 2, pp. 320-328.
Mesa et al. Emerging drugs for the therapy of primary and post essential thrombocythemia, post polycythemia vera myelofibrosis; Expert Opinion on Emerging Drugs; England, 2009, vol. 14, No. 3, pp. 471-479.
Vannucchi et al: RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF); Blood, 2009, vol. 114, No. 22, Abstract 307, p. 130 (2 pages).
Vannucchi et al: The mTOR Inhibitor, RAD001, Inhibits the Growth of Cells From Patients with Myeloproliferative neoplasms; Blood; 2009, vol. 114, No. 22, Abstract 2914, p. 1139 (2 pages).
Vannucchi et al: Inhibitors of PI3K/Akt and/or mTOR Inhibit the Growth of Cells of Myeloproliferative neoplasms and Synergize with JAK2 Inhibitor and Interferon; Blood; 2011, vol. 118, No. 21, pp. 1638-1639.

\* cited by examiner

MTOR/JAK INHIBITOR COMBINATION THERAPY

RELATED APPLICATIONS

This application claims priority to U.S. Provisional Patent Applications 61/444,581, filed Feb. 18, 2011, 61/503,789, filed Jul. 1, 2011, and 61/503,785, filed Jul. 1, 2011, the contents of which are hereby incorporated by reference in their entireties. The contents of any patents, patent applications, and references cited throughout this specification are hereby incorporated by reference in their entireties.

BACKGROUND

Myeloproliferative neoplasms (MPNs) are a group of disorders that cause an overproduction of blood cells (platelets, white blood cells and red blood cells) in the bone marrow. MPNs include polycythemia vera (PV), primary or essential thrombocythemia (ET), primary or idiopathic myelofibrosis, chronic myelogenous (myelocytic) leukemia (CML), chronic neutrophilic leukemia (CNL), juvenile myelomonocytic leukemia (JML) and chronic eosinophilic leukemia (CEL)/hyper eosinophilic syndrome (HES). These disorders are grouped together because they share some or all of the following features: involvement of a multipotent hematopoietic progenitor cell, dominance of the transformed clone over the non-transformed hematopoietic progenitor cells, overproduction of one or more hematopoietic lineages in the absence of a definable stimulus, growth factor-independent colony formation in vitro, marrow hypercellularity, megakaryocyte hyperplasia and dysplasia, abnormalities predominantly involving chromosomes 1, 8, 9, 13, and 20, thrombotic and hemorrhagic diatheses, exuberant extramedullary hematopoiesis, and spontaneous transformation to acute leukemia or development of marrow fibrosis but at a low rate, as compared to the rate in CML. The incidence of MPNs varies widely, ranging from approximately 3 per 100,000 individuals older than 60 years annually for CML to 0.13 per 100,000 children from birth to 14 years annually for JML (Vardiman J W et al., Blood 100 (7): 2292-302, 2002).

Accordingly, there remains a need for new treatments of MPNs, as well as other cancers.

SUMMARY OF THE INVENTION

Provided herein is a combination therapy comprising an mTOR inhibitor and a JAK inhibitor. The combination therapy is useful for the treatment of a variety of cancers, including MPNs. The combination therapy is also useful for the treatment of any number of JAK-associated diseases.

Accordingly, in one aspect, provided herein is a combination therapy comprising an mTOR inhibitor and a JAK inhibitor. In one embodiment, the JAK inhibitor has the general formula set forth in formula I:

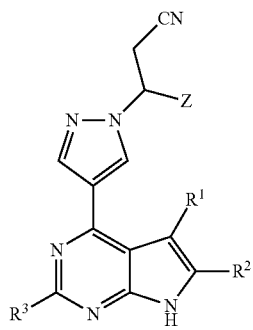

(I)

or stereoisomers, tautomers, racemates, solvates, metabolites, or pharmaceutically acceptable salts thereof. In another aspect, provided herein is a composition comprising an mTOR inhibitor and a JAK inhibitor. In a particular embodiment, the compound of formula I is (3R)-3-cyclopentyl-3-[4-(7H-pyrrolo[2,3-d]pyrimidin-4-yl)-1H-pyrazol-1-yl]propanenitrile (Compound A), or a pharmaceutically acceptable salt thereof.

In another embodiment, the JAK inhibitor is 5-Chloro-$N^2$-[(1S)-1-(5-fluoropyrimidin-2-yl)ethyl]-$N^4$-(5-methyl-1H-pyrazol-3-yl)-pyrimidine-2,4-diamine (AZD1480), or a pharmaceutically acceptable salt thereof.

In another embodiment the mTOR inhibitor is Everolimus (RAD001) or 2-(4-amino-1-isopropyl-1H-pyrazolo[3,4-d]pyrimidin-3-yl)-1H-indol-5-ol (PP242).

In one particular embodiment, the combination therapy comprises Everolimus and Compound A, or a pharmaceutically acceptable salt thereof. In another particular embodiment, the combination therapy comprises PP242 and Compound A, or a pharmaceutically acceptable salt thereof.

In one embodiment of the combination therapy provided herein, the mTOR inhibitor and the JAK inhibitor (e.g., a compound of formula I (e.g., Compound A, or a pharmaceutically acceptable salt thereof)) are in a single formulation or unit dosage form. The single formulation or unit dosage form can further comprise a pharmaceutically acceptable carrier. In another embodiment, the mTOR inhibitor and the JAK inhibitor are administered separately.

The combination therapy provided herein is useful for the treatment of a JAK-associated disease in a subject. Accordingly, in one aspect, provided herein is a method of treating cancer in a subject in need thereof comprising administering to the subject an effective amount of an mTOR inhibitor and a JAK inhibitor (e.g., a compound of formula I (e.g., Compound A, or a pharmaceutically acceptable salt thereof)). In one embodiment, the cancer is a myeloproliferative neoplasm. Non-limiting examples of myeloproliferative neoplasms that can be treated using the combination therapy of the invention include, but are not limited to, chronic myeloid leukemia (CML), polycythemia vera (PV), essential thrombocythemia (ET), primary or idiopathic myelofibrosis (PMF), chronic neutrophilic leukemia, chronic eosinophilic leukemia, chronic myelomonocytic leukemia, juvenile myelomonocytic leukemia, hypereosinophilic syndrome, systemic mastocytosis, and atypical chronic myelogenous leukemia. In another embodiment, the combination therapy can be used for treatment of intermediate or high-risk myelofibrosis, including primary myelofibrosis, post-polycythemia vera myelofibrosis or post-essential thrombocythemia myelofibrosis.

In one embodiment of these treatment methods, the subject is human. In another embodiment, the treatment comprises co-administering an mTOR inhibitor and a JAK inhibitor (e.g., a compound of formula I (e.g., Compound A, or a pharmaceutically acceptable salt thereof)). In another embodiment, the mTOR inhibitor and the JAK inhibitor (e.g., a compound of formula I (e.g., Compound A, or a pharmaceutically acceptable salt thereof)) are in a single formulation or unit dosage form. The mTOR inhibitor and the JAK inhibitor (e.g., a compound of formula I (e.g., Compound A, or a pharmaceutically acceptable salt thereof)) can be in separate formulations or unit dosage forms. In still another embodiment, the treatment comprises administering the mTOR inhibitor and the JAK inhibitor (e.g., a compound of formula I (e.g., Compound A, or a pharmaceutically acceptable salt thereof)) at substantially the same time, or different times. In another embodiment of the method, the mTOR inhibitor is administered to the subject, followed by administration of the JAK inhibitor (e.g., a compound of formula I (e.g., Compound A, or a pharmaceutically acceptable salt thereof)). In still another embodiment, the JAK inhibitor (e.g., a compound of formula I (e.g., Compound A, or a pharmaceutically acceptable salt thereof)) is administered to the subject, followed by administration of the mTOR inhibitor. In another embodiment of the method, the mTOR inhibitor and/or the JAK inhibitor (e.g., a compound of formula I (e.g., Compound A, or a pharmaceutically acceptable salt thereof)) is administered at amounts that would not be effective when one or both of the mTOR inhibitor and the JAK inhibitor (e.g., a compound of formula I (e.g., Compound A, or a pharmaceutically acceptable salt thereof)) is administered alone, but which amounts are effective in combination.

The combination therapy provided herein is also useful for inhibiting STAT5 phosphorylation. The STAT5 phosphorylation can be inhibited in a subject in need to thereof. In one embodiment, the inhibition of STAT5 phosphorylation in a subject treats a myeloproliferative neoplasm in the subject. The myeloproliferative neoplasm can be selected from the group consisting of chronic myeloid leukemia (CML), polycythemia vera (PV), essential thrombocythemia (ET), primary or idiopathic myelofibrosis (PMF), chronic neutrophilic leukemia, chronic eosinophilic leukemia, chronic myelomonocytic leukemia, juvenile myelomonocytic leukemia, hypereosinophilic syndrome, systemic mastocytosis, and atypical chronic myelogenous leukemia.

In another aspect, provided herein is a method of treating a myeloproliferative neoplasm comprising administering to a subject in need thereof. Everolimus and Compound A, or a pharmaceutically acceptable salt thereof. In another aspect, provided herein is a method of treating a myeloproliferative neoplasm comprising administering to a subject in need thereof PP242 and Compound A, or a pharmaceutically acceptable salt thereof. In one embodiment of these aspects, the myeloproliferative neoplasm is primary myelofibrosis, post-polycythemia vera myelofibrosis or post-essential thrombocythemia myelofibrosis.

BRIEF DESCRIPTION OF DRAWINGS

FIGS. 1B-1E show the effect of selected mTOR inhibitors, a JAK1/JAK2 inhibitor, histone deacetylase inhibitors and hydroxyurea on cell apoptosis and cell cycle in SET2 or HEL cells. The percentage of Annexin V-positive apoptotic cells was measured by flow cytometry in SET2 cells that had been exposed for 48 h to varying amounts of the indicated compound. Results are expressed ad percent viable cells compared to control wells containing vehicle (DMSO) only. The fraction of necrotic cells was identified as the double-positive Annexin V/propidium iodide cells. FIG. 1B shows the effect of mTOR inhibitors, RAD001 and PP242, on cell apoptosis and cell cycle. FIG. 1C shows the effect of a JAK1/JAK2 inhibitor, Compound A, on cell apoptosis and cell cycle. FIG. 1D shows the effect of a histone deacetylase inhibitor (HDAC), Panobinostat, on cell apoptosis and cell cycle. FIG. 1E shows the effect of hydroxyurea on cell apoptosis and cell cycle.

FIG. 2 shows the effect of selected mTOR inhibitors, a JAK1/JAK2 inhibitor, histone deacetylase inhibitors and hydroxyurea on mTOR and JAK/STAT signaling in SET2 cells. SET2 cells were incubated for 24 h with increasing concentrations of the drugs, and the level of total and phosphorylated JAK2, STAT5, and 4EBP1 was analyzed by western blot.

DETAILED DESCRIPTION

Figure 1C:
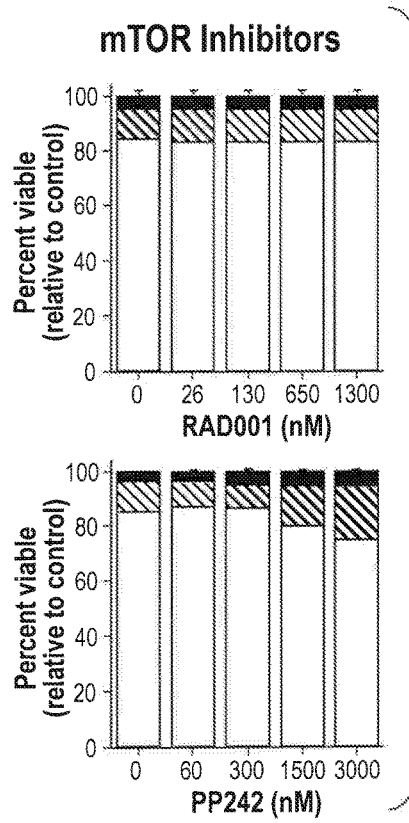
Figure 1C:
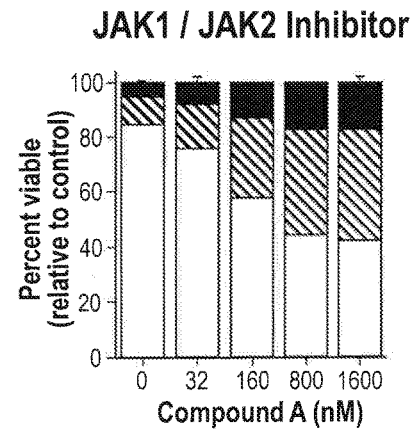
Figure 1D:
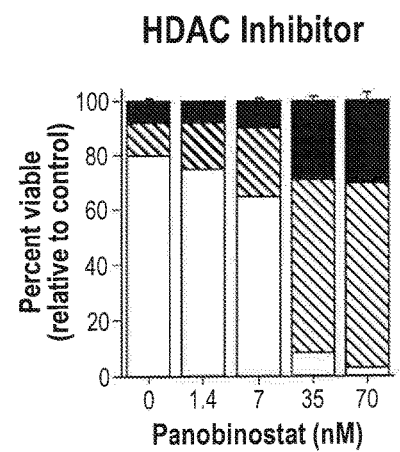

It has been discovered that administering a combination of an mTOR inhibitor and a JAK kinase inhibitor (e.g., a JAK kinase inhibitor of the formula I (e.g., Compound A, or a pharmaceutically acceptable salt thereof)) provides surprising, synergistic effects for treating cancer, e.g., myeloproliferative neoplasms (MPNs), in a subject. Such an approach—combination or co-administration of the two types of agents—can be useful for treating individuals suffering from cancer who do not respond to or are resistant to currently-available therapies. The combination therapy provided herein is also useful for improving the efficacy and/or reducing the side effects of currently-available cancer therapies for individuals who do respond to such therapies.

Certain terms used herein are described below. Compounds of the present invention are described using standard nomenclature. Unless defined otherwise, all technical and scientific terms used herein have the same meaning as is commonly understood by one of skill in the art to which this invention belongs.

mTOR Inhibitor/JAK Inhibitor Combination

Provided herein is a combination of therapeutic agents and administration methods for the combination of agents to treat cancer, e.g., MPNs. As used herein, a "combination of agents" and similar terms refer to a combination of two types of agents: (1) an mTOR inhibitor and (2) a JAK inhibitor (e.g., a JAK kinase inhibitor of the formula I (e.g., Compound A, or a pharmaceutically acceptable salt thereof)).

The mammalian target of rapamycin, commonly known as mTOR, is a serine/threonine protein kinase that regulates cell growth, cell proliferation, cell motility, cell survival, protein synthesis, and transcription. mTOR is a key intermediary in multiple mitogenic signaling pathways and plays a central role in modulating proliferation and angiogenesis in normal tissues and neoplastic processes. Hyperactivation of mTOR signaling has been implicated in tumorigenesis, and studies in several tumor types suggest that the anti-proliferative and anti-angiogenic properties of mTOR inhibitors are useful in cancer therapy. mTOR exists within two complexes, mTORC1 and mTORC2. mTORC1 is sensitive to rapamycin analogs (such as temsirolimus or everolimus) and mTORC2 is largely rapamycin-insensitive. Several mTOR inhibitors have been or are being evaluated in clinical trials for the treatment of cancer.

As used herein, the term "mTOR inhibitor" refers to a compound or a ligand that inhibits at least one activity of an mTOR, such as the serine/threonine protein kinase activity on at least one of its substrates (e.g., p70S6 kinase 1, 4E-BP1, AKT/PKB and eEF2). A person skilled in the art can readily determine whether a compound, such as rapamycin or an analogue or derivative thereof, is an mTOR inhibitor. Methods of identifying such compounds or ligands are known in the art. Examples of mTOR inhibitors include, without limitation, rapamycin (sirolimus), rapamycin derivatives, CI-779, everolimus (Certican™), ABT-578, tacrolimus (FK 506), ABT-578, AP-23675, BEZ-235, OSI-027, QLT-0447, ABI-009, BC-210, salirasib, TAFA-93, deforolimus (AP-23573), temsirolimus (Torisel™), 2-(4-Amino-1-isopropyl-1H-pyrazolo[3,4-d]pyrimidin-3-yl)-1H-indol-5-ol (PP242) and AP-23841.

As used herein, the term "selective mTOR inhibitor" refers to a compound or a ligand that inhibits mTOR activity but does not inhibit PI3K activity. Suitable selective mTOR inhibitors include RAD001. Accordingly, in one aspect, provided herein is a combination therapy comprising a selective mTOR inhibitor and a JAK inhibitor.

Rapamycin is a known macrolide antibiotic produced by *Streptomyces hygroscopicus*. Suitable derivatives of rapamycin include e.g., compounds of formula II:

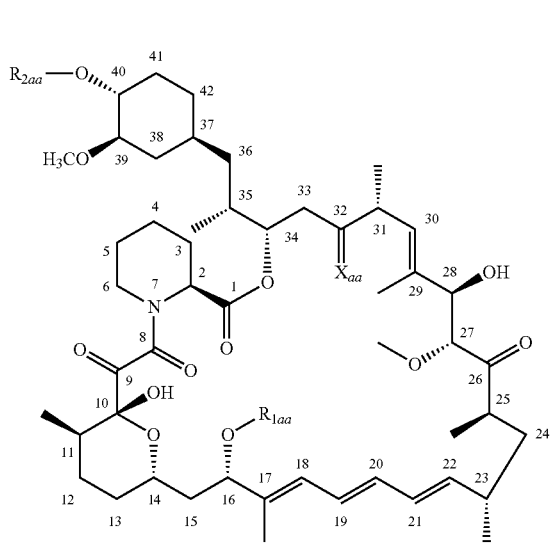

wherein
$R_{1aa}$ is $CH_3$ or $C_{3-6}$alkynyl,
$R_{2aa}$ is H or —$CH_2$—$CH_2$—OH, 3-hydroxy-2-(hydroxymethyl)-2-methyl-propanoyl or tetrazolyl, and
$X_{aa}$ is =O, (H,H) or (H,OH)
or a prodrug thereof when $R_{2aa}$ is —$CH_2$—$CH_2$—OH, e.g., a physiologically hydrolysable ether thereof.

Compounds of formula II are disclosed, e.g., in WO 94/09010, WO 95/16691, WO 96/41807, U.S. Pat. No. 5,362,718 and WO 99/15530, which are incorporated herein by reference. They may be prepared using the procedures described in these references.

Representative rapamycin derivatives of formula II are, e.g., 32-deoxorapamycin, 16-pent-2-ynyloxy-32-deoxorapamycin, 16-pent-2-ynyloxy-32(S or R)-dihydro-rapamycin, 16-pent-2-ynyloxy-32(S or R)-dihydro-40-O-(2-hydroxyethyl)-rapamycin, 40-[3-hydroxy-2-(hydroxymethyl)-2-methylpropanoate]-rapamycin (also called CCI779) or 40-epi-(tetrazolyl)-rapamycin (also called ABT578). Rapamycin derivatives may also include the so-called rapalogs, e.g., as disclosed in WO 98/02441 and WO 01/14387, e.g. AP23573, AP23464, AP23675 or AP23841. Further examples of a rapamycin derivative are those disclosed under the name TAFA-93 (a rapamycin prodrug), biolimus-7 or biolimus-9.

In a preferred embodiment, the mTOR inhibitor used in the combination therapy provided herein is Everolimus (RAD001) or 2-(4-amino-1-isopropyl-1H-pyrazolo[3,4-d]pyrimidin-3-yl)-1H-indol-5-ol (PP242) (see, e.g., Apsel et al., Nature Chemical Biology 4, 691-699 (2008)).

The JAK family plays a role in the cytokine-dependent regulation of proliferation and function of cells involved in immune response. Currently, there are four known mammalian JAK family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2). The JAK proteins range in size from 120 to 140 kDa and comprise seven conserved JAK homology (JH) domains; one of these is a functional catalytic kinase domain, and another is a pseudokinase domain potentially serving a regulatory function and/or serving as a docking site for STATs (Scott, M. J., C. J. Godshall, et al. (2002) Clin Diagn Lab Immunol 9(6): 1153-9).

As used herein, a "JAK inhibitor" refers to a compound or a ligand that inhibits at least one activity of a JAK kinase. A "JAK inhibitor" can also be a "JAK1/JAK2 inhibitor." In certain embodiments, the JAK inhibitor induces a JAK-inhibited state. Examples of JAK inhibitors include compounds of formula I and AZD1480.

The compound of formula I is defined as follows:

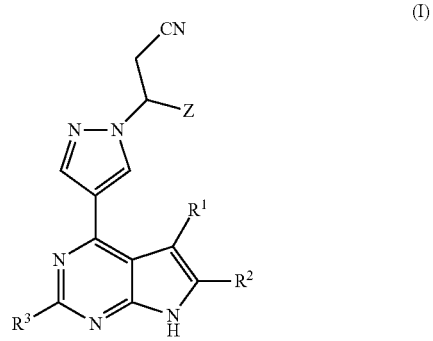

or stereoisomers, tautomers, racemates, solvates, metabolites, or pharmaceutically acceptable salts thereof,
wherein
$R^1$, $R^2$ and $R^3$ are independently selected from H, halo, and $C_{1-4}$ alkyl; and
Z is $C_{3-6}$ cycloalkyl (e.g., cyclopentyl).

Examples of compounds of formula I include the compounds described in U.S. U.S. Pat. No. 7,598,257, which is incorporated herein by reference in its entirety. Methods of making compounds of formula I, including Compound A, can be found in U.S. Pat. No. 7,598,257 and PCT Publication WO/2010/083283 (PCT/US2010/021003), both of which are incorporated herein by reference in their entireties.

In a particular embodiment, the compound of formula I is 3-cyclopentyl-3-[4-(7H-pyrrolo[2,3-d]pyrimidin-4-yl)-1H-pyrazol-1-yl]propanenitrile or a pharmaceutically acceptable salt thereof. In another embodiment, the compound of formula I is (3R)-3-cyclopentyl-3-[4-(7H-pyrrolo[2,3-d]pyrimidin-4-yl)-1H-pyrazol-1-yl]propanenitrile (Compound A) or a pharmaceutically acceptable salt thereof. In still another embodiment, the compound of formula I is (3S)-3-cyclopentyl-3-[4-(7H-pyrrolo[2,3-d]pyrimidin-4-yl)-1H-pyrazol-1-yl]propanenitrile or a pharmaceutically acceptable salt thereof. The synthesis of these compounds are described in, for example, U.S. Pat. No. 7,598,257 and PCT Publication WO/2010/083283 (PCT/US2010/021003).

In another embodiment, the compound of formula I is (3R)-3-cyclopentyl-3-[4-(7H-pyrrolo[2,3-d]pyrimidin-4-yl)-1H-pyrazol-1-yl]propanenitrile maleic acid salt. In still another embodiment, the compound of formula I is (3R)-3-cyclopentyl-3-[4-(7H-pyrrolo[2,3-d]pyrimidin-4-yl)-1H- pyrazol-1-yl]propanenitrile sulfuric acid salt. In yet another embodiment, the compound is of formula I is (3R)-3-cyclopentyl-3-[4-(7H-pyrrolo[2,3-d]pyrimidin-4-yl)-1H-pyrazol-1-yl]propanenitrile phosphoric acid salt ("phosphoric acid salt of Compound A"). The synthesis of these compounds are described in, for example, U.S. patent application Ser. No. 12/137,892, which is incorporated herein by reference in its entirety.

In an embodiment, provided herein is a combination therapy comprising the phosphoric acid salt of Compound A and an mTOR inhibitor, e.g., Everolimus or PP242.

As used herein, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl.

As used herein, the term "$C_{3-6}$ cycloalkyl" refers to saturated or unsaturated monocyclic or bicyclic hydrocarbon groups of 3-6 carbon atoms, preferably 5 carbon atoms. Exemplary monocyclic hydrocarbon groups include, but are not limited to, cyclopropyl, cyclobutyl, and cyclopentyl.

The term "halogen" or "halo" refers to chloro, bromo, fluoro, and iodo groups.

Agents may contain one or more asymmetric elements such as stereogenic centers or stereogenic axes, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms; all isomeric forms of the compounds are included in the present invention. In these situations, the single enantiomers (optically active forms) can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Unless otherwise specified, or clearly indicated by the text, reference to compounds useful in the combination therapy of the invention includes both the free base of the compounds, and all pharmaceutically acceptable salts of the compounds.

As used herein, the term "pharmaceutically acceptable salts" refers to the nontoxic acid or alkaline earth metal salts of the pyrimidine compounds of the invention. These salts can be prepared in situ during the final isolation and purification of the pyrimidine compounds, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methanesulfonate, nicotinate, 2-naphth-alenesulfonate, oxalate, pamoate, pectinate, persulfate, 3-phenylpropionate, picrate, pivalate, propionate, succinate, sulfate, tartrate, thiocyanate, p-toluenesulfonate, and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, hydroboric acid, nitric acid, sulfuric acid and phosphoric acid and such organic acids as formic acid, acetic acid, trifluoroacetic acid, fumaric acid, tartaric acid, oxalic acid, maleic acid, methanesulfonic acid, succinic acid, malic acid, methanesulfonic acid, benzenesulfonic acid, and p-toluenesulfonic acid, citric acid, and acidic amino acids such as aspartic acid and glutamic acid.

Provided herein is a combination therapy comprising an mTOR inhibitor and a JAK inhibitor (e.g., the JAK inhibitor of formula I (e.g., Compound A, or a pharmaceutically acceptable salt thereof). Administration of the combination (i.e., a combination of an mTOR inhibitor and a JAK inhibitor (e.g., the JAK inhibitor of formula I (e.g., Compound A, or a pharmaceutically acceptable salt thereof)) includes administration of the combination in a single formulation or unit dosage form, administration of the individual agents of the combination concurrently but separately, or administration of the individual agents of the combination sequentially by any suitable route. The dosage of the individual agents of the combination may require more frequent administration of one of the agent(s) as compared to the other agent(s) in the combination. Therefore, to permit appropriate dosing, packaged pharmaceutical products may contain one or more dosage forms that contain the combination of agents, and one or more dosage forms that contain one of the combination of agents, but not the other agent(s) of the combination.

The term "single formulation" as used herein refers to a single carrier or vehicle formulated to deliver effective amounts of both therapeutic agents to a patient. The single vehicle is designed to deliver an effective amount of each of the agents, along with any pharmaceutically acceptable carriers or excipients. In some embodiments, the vehicle is a tablet, capsule, pill, or a patch. In other embodiments, the vehicle is a solution or a suspension.

The term "unit dose" is used herein to mean simultaneous administration of both agents together, in one dosage form, to the patient being treated. In some embodiments, the unit dose is a single formulation. In certain embodiments, the unit dose includes one or more vehicles such that each vehicle includes an effective amount of at least one of the agents along with pharmaceutically acceptable carriers and excipients. In some embodiments, the unit dose is one or more tablets, capsules, pills, or patches administered to the patient at the same time.

The term "treat" is used herein to mean to relieve, reduce or alleviate, at least one symptom of a disease in a subject. Within the meaning of the present invention, the term "treat" also denotes, to arrest, delay the onset (i.e., the period prior to clinical manifestation of a disease or symptom of a disease) and/or reduce the risk of developing or worsening a symptom of a disease.

The term "subject" is intended to include animals. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer, e.g., myeloproliferative neoplasms.

The term "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, or in separate containers (e.g., capsules) for each active ingredient. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination of agents described herein display a synergistic effect. The term "synergistic effect" as used herein, refers to action of two agents such as, for example, an mTOR inhibitor and a JAK inhibitor (e.g., a JAK inhibitor of formula I), producing an effect, for example, slowing the symptomatic progression of cancer or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

In an embodiment, provided herein is a combination therapy comprising an effective amount of a JAK inhibitor and an mTOR inhibitor. An "effective amount" of a combination of agents (i.e., an mTOR inhibitor and a JAK inhibitor (e.g., a JAK inhibitor of formula I)) is an amount sufficient to provide an observable improvement over the baseline clinically observable signs and symptoms of the disorders treated with the combination.

An "oral dosage form" includes a unit dosage form prescribed or intended for oral administration.

Methods of Treatment Using an mTOR Inhibitor/JAK Inhibitor Combination

The invention provides a method of treating JAK-associated diseases, e.g., cancer, e.g., myeloproliferative neoplasms, in an individual by administering to the individual a combination of an mTOR inhibitor and a JAK inhibitor (e.g., a JAK inhibitor of formula I).

In one embodiment, provided herein are methods of treating a JAK-associated disease or disorder in a subject (e.g., patient) by administering to the individual in need of such treatment a therapeutically effective amount or dose of a combination of the present invention or a pharmaceutical composition thereof. A JAK-associated disease can include any disease, disorder or condition that is directly or indirectly linked to expression or activity of the JAK, including over-expression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, type I diabetes, lupus, psoriasis, inflammatory bowel disease, ulcerative colitis, Crohn's disease, myasthenia gravis, immunoglobulin nephropathies, autoimmune thyroid disorders, and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, atopic dermatitis and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, the skin disorder is treated by topical administration of the combination therapy.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma etc.), hematological cancers (e.g., lymphoma, leukemia such as acute lymphoblastic leukemia, or multiple myeloma), and skin cancer such as cutaneous T-cell lymphoma (CTCL) and cutaneous B-cell lymphoma. Example cutaneous T-cell lymphomas include Sezary syndrome and mycosis fungoides.

JAK-associated diseases can further include those characterized by expression of a mutant JAK2 such as those having at least one mutation in the pseudo-kinase domain (e.g., JAK2V617F).

JAK-associated diseases can further include myeloproliferative disorders (MPDs) such as polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), systemic mast cell disease (SMCD), and the like.

Further JAK-associated diseases include inflammation and inflammatory diseases. Example inflammatory diseases include inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases.

The combination therapy described herein can further be used to treat ischemia reperfusion injuries or a disease or condition related to an inflammatory ischemic event such as stroke or cardiac arrest. The combination therapy described herein can further be used to treat anorexia, cachexia, or fatigue such as that resulting from or associated with cancer. The combination therapy described herein can further be used to treat restenosis, sclerodermitis, or fibrosis. The combination therapy described herein can further be used to treat conditions associated with hypoxia or astrogliosis such as, for example, diabetic retinopathy, cancer, or neurodegeneration. See, e.g., Dudley, A. C. et al. Biochem. J. 2005, 390(Pt 2):427-36 and Sriram, K. et al. J. Biol. Chem. 2004, 279(19):19936-47. Epub 2004 Mar. 2.

The chronic myeloproliferative neoplasms (MPN), which include polycythemia vera (PV), essential thrombocythemia (ET) and primary myelofibrosis (PMF), are characterized by a V617F point mutation in exon 14 of Janus Kinase 2 (JAK2) occurring in greater than 95% of PV and 60% of ET or PMF patients. Other JAK2 exon 12 mutations are detected in rare patients with PV while mutations in MPL have been reported in 5-10% of ET or PMF patients (Vannucchi A M, Guglielmelli, P, Tefferi, A. Advances in understanding and management of myeloproliferative neoplasms. AC—A Cancer Journal for Clinicians. 2009; 59:171-191). These molecular abnormalities are all associated with constitutive activation of the JAK/signal transducer and activator of transcription (STAT) signaling pathway and contribute to cytokine hypersensitivity and cytokine independent growth of the mutant cells, as exemplified by the erythropoietin-independent erythroid colonies (EEC). Transplantation of JAK2V617F-overexpressing hematopoietic cells in mice is sufficient to recapitulate a PV phenotype, that in some models evolved to myelofibrosis. A MPN disorder with the phenotype of PV or ET has been obtained also in conditional knock-in mice. Dysregulation of the JAK/STAT pathway is associated with development of solid and hematological cancers and constitutively activated STAT5A or STAT5B mutants (caSTAT5) display oncogenic properties in vitro and in vivo. In aggregate, JAK2 represents a potentially valuable therapeutic target in MPN patients (Id.), as supported by effects in murine models of MPN and current evidence in clinical trials.

Activation of other downstream pathways through the phosphatidylinositol 3-kinase (PI3K) and extracellular signal-regulated kinase (ERK) has been documented in JAK2V617F mutated cells. The serine/threonine protein kinase B/Akt is downstream of PI3K; it is a key regulator of many cellular processes including cell survival, proliferation and differentiation, and is commonly dysregulated in cancer cells. Although Akt resulted constitutively activated in JAK2V617F mutated cells in vitro and in V617F transgenic or knock-in mice (Akada H, Yan D, Zou H, Fiering S, Hutchison R E, Mohi M G. Conditional expression of heterozygous or homozygous Jak2V617F from its endogenous promoter induces a polycythemia vera-like disease. Blood. 2010; 115:3589-3597), the contribution of PI3K/Akt signaling to the pathogenesis of MPN is still poorly characterized. Akt is phosphorylated and activated via PI3K in response to ligand-engagement of the erythropoietin (EPO) receptor and has a role in normal erythroid differentiation. In particular, Akt is able to support erythroid differentiation in JAK2-deficient fetal liver progenitor cells through a mechanism downstream of EpoR and at least in part related to GATA-1 phosphorylation. Akt resulted activated in erythroblasts from the bone marrow or the spleen of mice with conditional JAK2V617F knock-in allele, especially in V617F homozygous animals. Comparably increased phosphorylation of STAT5 and Akt was demonstrated by immunocytochemistry in the bone marrow of MPN patients, particularly in megakaryocytes. The preferential activation of Akt in megakaryocytes may be reconciled with the strong inhibition of human megakaryocyte progenitors' proliferation after blockade of mTOR signaling by rapamycin. Furthermore, small molecule inhibitors of the JAK/STAT or PI3K/Akt pathway caused comparable inhibition of spontaneous and EPO-induced erythroid differentiation in cultured PV progenitor cells.

Accordingly, in a certain embodiment, the cancer that can be treated using the combination provided herein is a myeloproliferative disorder. Myeloproliferative disorders (MPDs), now commonly referred to as meyloproliferative neoplasms (MPNs), are in the class of haematological malignancies that are clonal disorders of hematopoietic progenitors. Tefferi, A. and Vardiman, J. W., Classification and diagnosis of myeloproliferative neoplasms: The 2008 World Health Organization criteria and point-of-care diagnostic algorithms, Leukemia, September 2007, 22: 14-22, is hereby incorporated by reference. They are characterized by enhanced proliferation and survival of one or more mature myeloid lineage cell types. This category includes but is not limited to, chronic myeloid leukemia (CML), polycythemia vera (PV), essential thrombocythemia (ET), primary or idiopathic myelofibrosis (PMF), chronic neutrophilic leukemia, chronic eosinophilic leukemia, chronic myelomonocytic leukemia, juvenile myelomonocytic leukemia, hypereosinophilic syndrome, systemic mastocytosis, and atypical chronic myelogenous leukemia. Tefferi, A. and Gilliland, D. G., Oncogenes in myeloproliferative disorders, Cell Cycle. March 2007, 6(5): 550-566 is hereby fully incorporated by reference in its entirety for all purposes.

In another embodiment, the combination therapy provided herein is useful for the treatment of primary myelofibrosis, post-polycythemia vera myelofibrosis, post-essential thrombocythemia myelofibrosis, and secondary acute myelogenous leukemia.

In another embodiment, the combination therapy provided herein can be used to treat patients with intermediate or high-risk myelofibrosis, including primary myelofibrosis, post-polycythemia vera myelofibrosis and post-essential thrombocythemia myelofibrosis.

In some embodiments, the subject to be treated (e.g., a human) is determined to be non-responsive or resistant to one or more therapies for myeloproliferative disorders.

In a particular embodiment, provided herein is a method of treating a myeloproliferative neoplasm in a subject in need thereof, comprising administering to the subject an effective amount of a composition comprising Everolimus and Compound A, or a pharmaceutically acceptable salt thereof.

In an embodiment, provided herein is the use of an mTor inhibitor and a JAK inhibitor in the manufacture of a medicament for the treatment of cancer, e.g., a myeloproliferative disorder, e.g., intermediate or high-risk myelofibrosis, including primary myelofibrosis, post-polycythemia vera myelofibrosis and post-essential thrombocythemia myelofibrosis.

In another embodiment, provided herein is a method of treating a myeloproliferative neoplasm in a subject in need thereof, comprising administering to the subject an effective amount of a composition comprising PP242 and Compound A, or a pharmaceutically acceptable salt thereof.

Provided herein are methods of treating disease, e.g., a myeloproliferative disorder, by administering an effective amount of a compound of an mTOR inhibitor and a JAK inhibitor to an individual suffering from a disease. The amount of the combination of agents is effective to treat the disease. It is important to note the synergistic effects of the combination of agents: even though one or more of the agents administered alone at a particular dosage may not be effective, when administered in combination, at the same dosage of each agent, the treatment is effective. The doses of the one or more of the agents in the combination therefore can be less than the FDA approved doses of each agent.

Dosages

The optimal dose of the combination of agents for treatment of disease can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art.

The amount of combination of agents that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage may vary depending on the compound used and the particular condition to be treated or prevented. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

The dosage form can be prepared by various conventional mixing, comminution and fabrication techniques readily apparent to those skilled in the chemistry of drug formulations.

The oral dosage form containing the combination of agents or individual agents of the combination of agents may be in the form of micro-tablets enclosed inside a capsule, e.g. a gelatin capsule. For this, a gelatin capsule as is employed in pharmaceutical formulations can be used, such as the hard gelatin capsule known as CAPSUGEL, available from Pfizer.

Many of the oral dosage forms useful herein contain the combination of agents or individual agents of the combination of agents in the form of particles. Such particles may be compressed into a tablet, present in a core element of a coated dosage form, such as a taste-masked dosage form, a press coated dosage form, or an enteric coated dosage form, or may be contained in a capsule, osmotic pump dosage form, or other dosage form.

The drug compounds of the present invention (for example, an mTOR inhibitor and a JAK inhibitor) are present in the combinations, dosage forms, pharmaceutical compositions and pharmaceutical formulations disclosed herein in a ratio in the range of 100:1 to 1:100. For example, the ratio of a compound of formula I:an mTOR inhibitor can be in the range of 1:100 to 1:1, for example, 1:100, 1:90, 1:80, 1:70, 1:60, 1:50, 1:40, 1:30, 1:20, 1:10, 1:5, 1:2, or 1:1 of formula I:an mTOR inhibitor. In another example, the ratio of an mTOR inhibitor:a compound of formula I can be in the range of 1:100 to 1:1, for example, 1:100, 1:90, 1:80, 1:70, 1:60, 1:50, 1:40, 1:30, 1:20, 1:10, 1:5, 1:2, or 1:1 of an mTOR inhibitor:a compound of formula I.

The optimum ratios, individual and combined dosages, and concentrations of the drug compounds that yield efficacy without toxicity are based on the kinetics of the active ingredients' availability to target sites, and are determined using methods known to those of skill in the art.

The pharmaceutical compositions or combinations provided herein (i.e., an mTOR inhibitor and a JAK inhibitor (e.g., a JAK inhibitor of formula I)) can be tested in clinical studies. Suitable clinical studies may be, for example, open label, dose escalation studies in patients with proliferative diseases. Such studies prove in particular the synergism of the active ingredients of the combination of the invention. The beneficial effects on proliferative diseases may be determined directly through the results of these studies which are known as such to a person skilled in the art. Such studies may be, in particular, suitable to compare the effects of a monotherapy using the active ingredients and a combination of the invention. In one embodiment, the dose of a compound of an mTOR inhibitor, e.g., Everolimus (RAD001) or PP242, is escalated until the Maximum Tolerated Dosage is reached, and a JAK inhibitor (e.g., a JAK inhibitor of formula I) is administered with a fixed dose. Alternatively, a JAK inhibitor (e.g., a JAK inhibitor of formula I), may be administered in a fixed dose and the dose of the mTOR inhibitor may be escalated. Each patient may receive doses of the compounds either daily or intermittently. The efficacy of the treatment may be determined in such studies, e.g., after 12, 18 or 24 weeks by evaluation of symptom scores every 6 weeks.

The administration of a combination therapy of the invention may result not only in a beneficial effect, e.g. a synergistic therapeutic effect, e.g. with regard to alleviating, delaying progression of or inhibiting the symptoms, but also in further surprising beneficial effects, e.g. fewer side-effects, an improved quality of life or a decreased morbidity, compared with a monotherapy applying only one of the pharmaceutically active ingredients used in the combination of the invention.

A further benefit may be that lower doses of the active ingredients of the combination of the invention may be used, for example, that the dosages need not only often be smaller but may also be applied less frequently, which may diminish the incidence or severity of side-effects. This is in accordance with the desires and requirements of the patients to be treated.

It is one objective of this invention to provide a pharmaceutical composition comprising a quantity, which may be jointly therapeutically effective at targeting or preventing cancer, e.g., a myeloproliferative disorder. In this composition, an mTOR inhibitor and a JAK inhibitor (e.g., a JAK inhibitor of formula I) may be administered together, one after the other or separately in one combined unit dosage form or in two separate unit dosage forms. The unit dosage form may also be a fixed combination.

The pharmaceutical compositions for separate administration of both compounds, or for the administration in a fixed combination, i.e. a single galenical composition comprising both compounds according to the invention may be prepared in a manner known per se and are those suitable for enteral, such as oral or rectal, and parenteral administration to mammals (warm-blooded animals), including humans, comprising a therapeutically effective amount of at least one pharmacologically active combination partner alone, e.g. as indicated above, or in combination with one or more pharmaceutically acceptable carriers or diluents, especially suitable for enteral or parenteral application.

Formulations

The drug combinations provided herein may be formulated by a variety of methods apparent to those of skill in the art of pharmaceutical formulation. The various release properties described above may be achieved in a variety of different ways. Suitable formulations include, for example, tablets, capsules, press coat formulations, and other easily administered formulations.

Suitable pharmaceutical formulations may contain, for example, from about 0.1% to about 99.9%, preferably from about 1% to about 60%, of the active ingredient(s). Pharmaceutical formulations for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount may be reached by administration of a plurality of dosage units.

In particular, a therapeutically effective amount of each of the combination partner of the combination of the invention may be administered simultaneously or sequentially and in any order, and the components may be administered separately or as a fixed combination. For example, the method of treating a disease according to the invention may comprise (i) administration of the first agent in free or pharmaceutically acceptable salt form and (ii) administration of the second agent in free or pharmaceutically acceptable salt form, simultaneously or sequentially in any order, in jointly therapeutically effective amounts, preferably in synergistically effective amounts, e.g. in daily or intermittently dosages corresponding to the amounts described herein. The individual combination partners of the combination of the invention may be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The effective dosage of each of the combination partners employed in the combination of the invention may vary depending on the particular compound or pharmaceutical composition employed, the mode of administration, the condition being treated, the severity of the condition being treated. Thus, the dosage regimen of the combination of the invention is selected in accordance with a variety of factors including the route of administration and the renal and hepatic function of the patient. A clinician or physician of ordinary skill can readily determine and prescribe the effective amount of the single active ingredients required to alleviate, counter or arrest the progress of the condition.

Preferred suitable dosages for the compounds used in the treatment described herein are on the order of about 1 mg to about 600 mg, preferably about 3, 5, 10, 15, 20, 25, 30, 35, 40, 45, 50, 55, 60, 65, 70, 75, 80, 90, 95, 100, 120, 140, 160, 180, 200, 220, 240, 260, 280, 300, 320, 340, 360, 380, 400, 420, 440, 460, 480, 500, 520, 540, 560, 580 to about 600 mgs total. In an embodiment, the JAK inhibitor is administered in a 5 mg, 10 mg, 15 mg, 20 mg, or a 25 mg dose.

Accordingly, in an embodiment, provided herein is a composition comprising an mTOR inhibitor and a compound of formula I. In an embodiment, the compound of formula I is (3R)-3-cyclopentyl-3-[4-(7H-pyrrolo[2,3-d]pyrimidin-4-yl)-1H-pyrazol-1-yl]propanenitrile, or a pharmaceutically acceptable salt thereof. In another embodiment, the mTOR inhibitor is Everolimus (RAD001) or 2-(4-Amino-1-isopropyl-1H-pyrazolo[3,4-d]pyrimidin-3-yl)-1H-indol-5-ol (PP242). In still another embodiment, the composition further comprises a pharmaceutically acceptable carrier.

Examples

The invention is further illustrated by the following examples. The examples should not be construed as further limiting.

Presented below is evidence that drugs targeting mTOR signaling prevented cytokine-induced and cytokine-independent cell proliferation in various cellular models of MPN and that simultaneous treatment with a JAK1/JAK2 inhibitor or interferon-α resulted in synergistic activity. These findings provide a rationale for exploring the effectiveness of targeting Akt/mTOR in the treatment of myeloproliferative neoplasms.

Methods and Materials
Reagents

RAD001 (an mTOR specific allosteric inhibitor), PP242 (an ATP domain inhibitor of mTOR) and hydroxyurea were obtained from Sigma-Aldrich (St. Louis, Germany). Interferon-α was obtained from Pegasys. Antibodies against phospho(p)-STAT5 (Tyr694), STAT5, p-4EBP1 (Thr70), 4EBP1, mTOR, p-JAK2 (Tyr1007/1008) and JAK2, were from Cell Signaling Technology (Danvers, Mass., US). Anti-human tubulin antibody was from Santa Cruz Biotechnology (Santa Cruz, Calif., US). Recombinant human IL-3, GM-CSF, SCF, and EPO were purchased from Miltenyi Biotec (Gladbach, Germany). siRNAs against mTOR were from Dharmacon siGENOME Smart pool (Thermo Scientific, Waltham, Mass., US); the siGENOME Non-Targeting siRNA Pool #1 (Thermo Scientific) was used as a negative control.

Cell Lines and Cell Culture

The HEL, SET2 and K562 human cell lines were purchased from the German Collection of Microorganisms and Cell Cultures (DSMZ, Braunschweig, Germany). Murine BaF/3 and BaF/3-EPOR cells expressing JAK2 wild-type (wt) or JAK2V617F were donated by R. Skoda (Basel, Switzerland). Cell lines were cultured in RPMI 1640 supplemented with 10% fetal bovine serum (FBS; Lonza, Belgium) (20% for SET2 cells), antibiotics and L-glutamine mIL-3 and EPO were added to the culture medium of JAK2 WT BaF/3 and BaF/3-EPOR cells, respectively.

Human Cells

Samples of peripheral blood (PB) or bone marrow (BM) were obtained from patients diagnosed with PV or PMF (2008 WHO criteria) under a protocol approved by Institutional Review Board of Azienda Ospedaliera-Universitaria Careggi and after obtaining an informed consent. Healthy donors of hematopoietic stem cells provided informed consent to donate excess $CD34^+$ cells. Research was carried out according to the principles of Declaration of Helsinki. $CD34^+$ cells were immunomagnetically selected as described. The JAK2V617F mutational status was determined by a quantitative real-time PCR assay in granulocytes.

Inhibition of Proliferation Assay, Clonogenic Assay, and Apoptosis or Cell Cycle Analysis Cells ($2 \times 10^4$) were plated in 96-well culture tissue plates with increasing concentrations of the drug(s), in triplicate; viable cells were assessed using the WST-1 assay (Roche, USA) and normalized to wells containing an equivalent volume of vehicle (DMSO) only. The concentration at which 50% inhibition of proliferation occurred ($IC_{50}$) was calculated using the Origin software (V 7.5, OriginLab Northampton, Mass.). In some experiments, clonogenic tests were also employed. Cells ($5\times10^3$) were plated in 0.5% agar in medium supplemented with FBS, and variable amount of the drug(s) (or an equivalent volume of vehicle in control plates) was added once at the beginning of culture. Colonies were enumerated by inverted microscopy after 7 day incubation. Quantification of apoptotic cells was accomplished by flow cytometry using the Annexin-V-FLUOS Staining kit (Roche); at least 20,000 events were acquired. For cell cycle distribution analysis by flow cytometry, $1\times10^6$ cells were treated with ethanol 95%, RNase 10 µg/mL and propidium iodide 50 mg/mL.

Colony Assays for Human Hematopoietic Progenitors and Colony Genotyping

BM mononuclear cells from MPN patients or control subjects were plated at $1\times10^5$/mL in methylcellulose (MethoCult; StemCell Technologies, Vancouver, Canada) supplemented with SCF 50 ng/mL, IL-3 10 ng/mL, IL-6 10 ng/mL, GM-CSF 10 ng/mL, G-CSF 10 ng/mL and EPO 3 U/mL for the growth of BFU-E and CFU-GM. EEC assay was performed by plating $2.5\times10^5$/mL PB mononuclear cells from PV patients in methylcellulose containing leukocyte-conditioned medium without EPO (StemCell Technol., cat. No. #04531). For the growth of CFU-Mk, $5\times10^4$/mL CD34$^+$ cells were plated in a 24-well plate in Megacult Collagen and medium with lipids (StemCell Technol.) supplemented with Thrombopoietin 50 ng/mL, IL-3 10 ng/mL, IL-6 10 ng/mL. Colonies were enumerated on day 14 according to standard criteria.

For JAK2V617F single-colony genotyping an allele-specific PCR assay was used. Well-separated colonies (at least 40 colonies per point) were individually plucked off the semisolid medium in 5 µL DNase/RNase-free water, lysed at 95° C. for 5 minutes, and subjected to PCR amplification and gel electrophoresis.

Cell Lysis and SDS-PAGE Western Blotting

Cells were resuspended in RIPA lysis buffer (50 mM pH 7.4 Tris-HCl, 150 mM NaCl, 1% NP-40, 1 mMEDTA) containing a proteinase inhibitor cocktail (Halt Protease Inhibitor Cocktail Kit, PIERCE, Rockford, Ill., US) and subjected to sodium dodecyl sulphate polyacrylamide gel electrophoresis separation and western blotting onto Immunoblot PVDF membrane (BioRad, Hercules, Calif., US), according to standard protocols. Membranes were probed with primary antibodies followed by horseradish peroxidase-conjugated anti-Ig antibody produced in rabbits (Sigma-Aldrich); immunoreactive proteins were revealed with ECL using the Image Quant 350 apparatus (GE Healthcare, Little Chalfont, UK).

RNA Isolation and Real-Time Quantitative PCR (RTQ-PCR)

Total RNA was purified using Trizol (Invitrogen-Life Technologies, Paisley, UK), and the RNA concentration and purity/integrity was determined with NanoDrop ND-1000 spectrophotometer (NanoDrop Techn., Wilmington, Del., USA). One microgram of RNA was reverse transcribed using High Capacity cDNA Archive Kit (Applied Biosystems, Foster City, Calif.). RT-QPCR reactions were performed with the TaqMan Universal PCR Master Mix using ABI PRISM 7300 HT and TaqMan® Gene Expression Assays (Applied Biosystems), in triplicate. Gene expression profiling was achieved using the Comparative cycle threshold ($C_T$) method of relative quantitation using VIC-labeled RNaseP probe as the housekeeping gene ($\Delta C_T$).

Cell Transfection

Exponentially growing HEL cells were electroporated with siRNAs in the Amaxa Nucleofector (Amaxa Biosystems, Gaithersburg, Md., USA) using Amaxa kit R. Briefly, $2-5\times10^6$ cells in 0.1 mL volume were transfected with 1 µM siRNA and immediately transferred to 24-well plates containing prewarmed culture medium. Transfection efficiency and cell viability were assessed by flow cytometry with pmaxGFP® (Amaxa Biosystems), and resulted always greater than 85%.

Statistical Methods

Comparison between groups was performed by the Mann-Whitney U or Fisher test as appropriate, using the SPSS (StatSoft, Inc., Tulsa, Okla.) or Origin software. The level of significance from two-sided tests was $P<0.05$. The combination index (CI), that is a measure of the interaction between two drugs, was calculated according to the median-effect principle of the Chou and Talalay method using the CalcuSyn software. According to this formula, when CI<1 the interaction of two drugs is considered synergistic, when CI=1 the interaction is additive, and when CI>1 the interaction is antagonistic.

Results mTOR Inhibitors Abrogate Proliferation of JAK2V617F Mutant Cell Lines

To ascertain whether JAK2V617F mutant human leukemia cell lines were sensitive to mTOR inhibition, the selective allosteric mTOR inhibitor RAD001 and the ATP competitive inhibitor of the active site of mTOR, PP242, were employed. It was discovered that JAK2V617F mutant HEL and SET2 cells were at least as sensitive to mTOR inhibition as the BCR/ABL positive K562 cells used as control. $IC_{50}$ values are shown in Table 1. The effects of mTOR inhibitors in JAK2 wild-type murine IL-3-dependent (Ba/F3) or EPO-dependent (Ba/F3-EPOR) cells or the cytokine-independent JAK2V617F counterpart were investigated. It was found that V617F Ba/F3 cells were more sensitive to RAD001 than the JAK2 wt counterpart either in the absence or the presence of IL-3 in the culture medium. Similarly, in Ba/F3-EPOR cells, the $IC_{50}$ of V617F mutant cells was 651 nM and 1,213 nM in the absence and presence of EPO, respectively, compared to an $IC_{50}>10,000$ nM in JAK2 wt cells. PP242 was similarly effective: in V617F Ba/F3 cells $IC_{50}$ was 800 nM and 1,600 nM, respectively, in the absence or presence of IL-3 versus 3,400 nM in wt cells; in wt Ba/F3-EPOR cells, $IC_{50}$ was 5,931 nM versus 500 nM and 750 nM in V617F cells supplemented or not with EPO, respectively (Table 1). At their $IC_{50}$ concentration, RAD001 and PP242 (not shown) caused cell cycle arrest of SET2 and HEL cells in the G0/G1 phase of the cell cycle. On the other hand, treatment with RAD001 was largely ineffective in inducing cell death, while PP242 promoted a modest, yet dose-dependent, cell apoptosis at highest concentrations in SET2 (FIG. 1B) or HEL (not shown) cells. In addition to inhibition of cell proliferation it was found that RAD001 also impaired the clonogenic potential of JAK2V617F mutant HEL, SET2 and UKE-1 cells more efficiently than K562. Also, colony formation by V617F Ba/F3 cells was inhibited at significantly lower RAD001 concentrations, irrespective of cytokine in the medium, than the wt counterpart (data not shown). Overall, these data indicate that JAK2V617F mutant cells are uniformly sensitive to mTOR inhibition and suggest that abrogation of cell proliferation reflects mainly a cytostatic rather than an apoptotic effect.

Figure 1E:
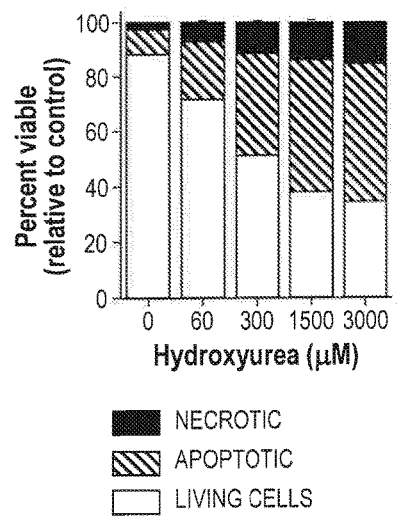

Next, the mechanisms of inhibition of cell proliferation induced by mTOR inhibitors with those of the JAK1/JAK2 inhibitor Compound A and the histone deacetylase (HDAC) inhibitor Panobinostat were compared. Those molecules were all growth inhibitory in HEL and SET2 cells at $IC_{50}$ concentrations significantly lower than those measured in K562 cell line (Table 1). However, unlike mTOR inhibitors, they were dose-dependently potent inducers of cell apoptosis (FIG. 1 C,D). HEL ($IC_{50}$=410 µM) and SET2 ($IC_{50}$=330 µM) cells resulted more sensitive to the ribonucleoside diphosphate reductase inhibitor hydroxyurea than K562 cells ($IC_{50}$=4,910 µM) (Table 1); hydroxyurea induced dose-dependent cell apoptosis (FIG. 1E).

The effect of the JAK1/JAK2 inhibitor was also evaluated in Ba/F3 cells to exploit the role of cytokine exposure to drug sensitivity. It was found that V617F Ba/F3 and Ba/F3-EPOR cells were more sensitive to Compound A ($IC_{50}$=34 nM and 220 nM, respectively) that their wt counterpart (1,600 nM or 457 nM for Compound A, respectively). However, addition of the appropriate cytokine to culture medium abrogated the preferential growth inhibitory effect of the JAK1/JAK2 inhibitor on V617F mutant cells ($IC_{50}$=1600 nM for Compound A, in Ba/F3 cells; $IC_{50}$=521 nM for Compound A, in Ba/F3-EPOR cells) (Table 1).

Overall, these data indicate that the growth inhibitory activity of JAK1/JAK2 and HDAC inhibitors in JAK2V617F leukemia cell lines is prevalently mediated by cell apoptosis. Furthermore, it was confirmed that cytokines markedly reduced the cell sensitivity to JAK1/JAK2 inhibitors.

FIG. 1 shows the effect of selected mTOR inhibitors, a JAK1/JAK2 inhibitor, histone deacethylase inhibitors and hydroxyurea on cell apoptosis and cell cycle in SET2 or HEL cells. In panels (B) to (E), the percentage of Annexin V-positive apoptotic cells was measured by flow cytometry in SET2 cells that had been exposed for 48 h to varying amount of the mTOR inhibitors RAD001 or PP242 (B), JAK1/JAK2 inhibitor Compound A (C), HDAC inhibitor Panobinostat (D) or hydroxyurea (E). Results are expressed ad percent viable cells compared to control wells containing vehicle (DMSO) only. The fraction of necrotic cells was identified as the double-positive Annexin V/ propidium iodide cells. One representative of three similar experiments. *, P<0.05; **, P<0.01.

Figure 2A:
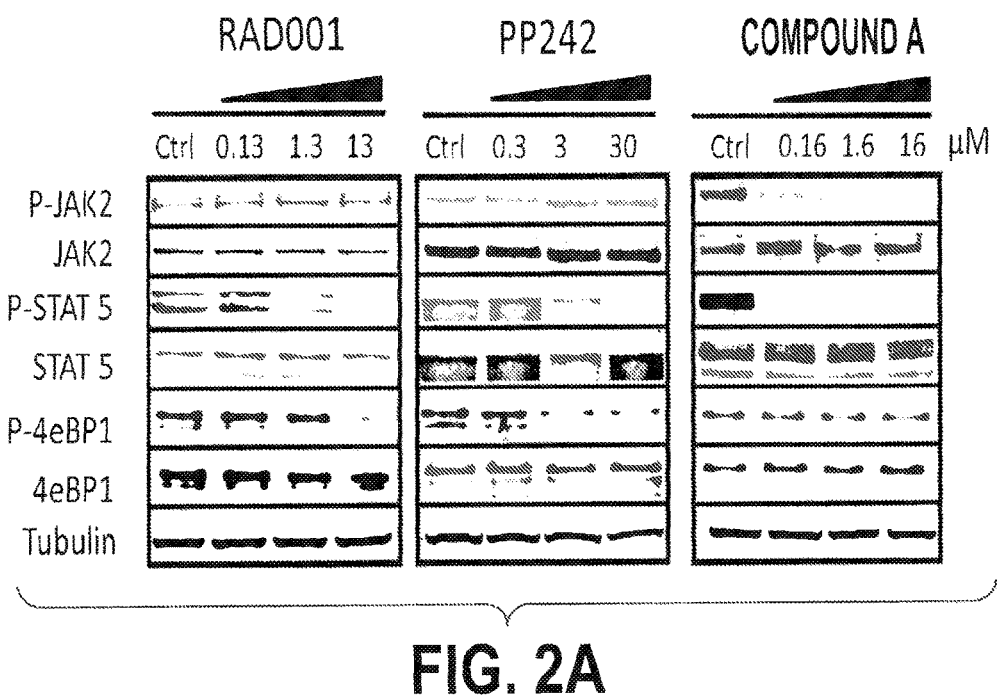
FIG. 2A shows the results for mTOR inhibitors, RAD001 and PP242, and a JAK1/JAK2 inhibitor, Compound A.
Figure 2B:
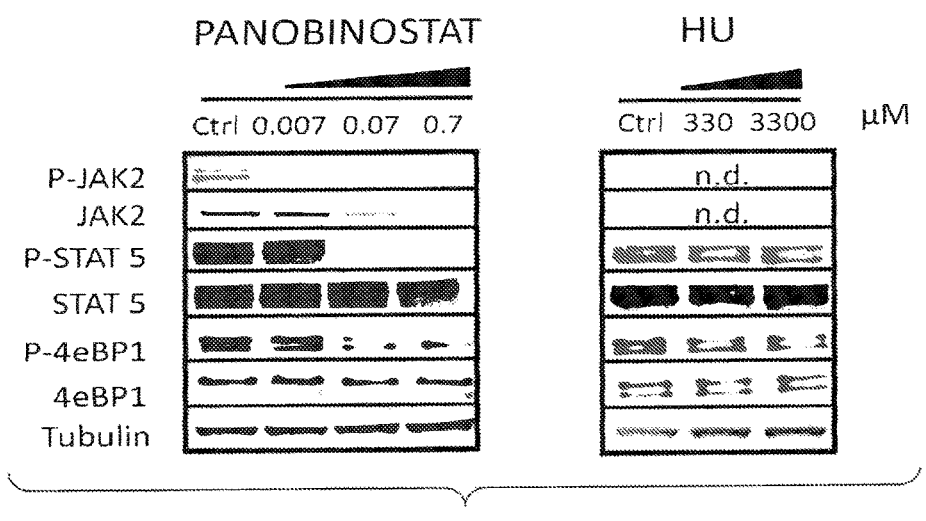
FIG. 2B shows the results for a histone deacethylase inhibitor (HDAC), Panobinostat, and hydroxyurea (HU).

Table 4 shows inhibition of clonogenic growth of JAK2V617F mutant cell lines by mTOR inhibitors, RAD001 or PP242 and JAK1/JAK2 inhibitor Compound A. JAK2V617F mutant human-origin cell lines, either heterozygous (SET-2) or homozygous (HEL), and the BCR/ABL mutant K562 cell line (used as a control), were exposed to increasing concentrations of RAD001, PP242 or Compound A. $10^3$ cells were plated in agar in the presence of variable amount of the drug; colonies were counted on day 7 and expressed as a percentage of colony number grown in control plates containing vehicle. Murine BaF/3 cells overexpressing JAK2V617F were similarly exposed to RAD001, PP242 or Compound A, and compared to wild-type cells (wt). Interleukin-3 (10 ng/mL) was added or not to the culture medium. $IC_{50}$ values shown are the Mean±SD of at least three independent experiments.

mTOR Inhibitors Attenuate Downstream Signalling of mTOR Pathway and Reduce STAT5 Phosphorylation in JAK2V617F Mutated Cell Lines The effect of mTOR inhibition on signal transduction in JAK2V617F mutant cells using SET2 cells as a model was investigated next (FIG. 2). It was observed that treatment with RAD001 and PP242 dose-dependently reduced phosphorylation of the mTOR target 4E-BP1 and, unexpectedly, of STAT5, while both phosphorylated and total JAK2 resulted unaffected. In comparison, the JAK1/JAK2 inhibitor Compound A markedly and dose-dependently reduced phosphorylation of JAK2 and STAT5 leaving unaffected 4EBP1. The HDAC inhibitor panobinostat dose-dependently reduced phosphorylated and total JAK2, phosphorylated STAT5 and showed a modest effect on phosphorylated 4E-BP1. Conversely, hydroxyurea did not affect the level or the phosphorylation status of 4EBP1 or STAT5.

To better characterize the correlation between JAK2V617F mutation and mTOR activation, as well as the consequences of mTOR inhibition on STAT5 phosphorylation, BA/F3 and Ba/F3-EPOR cells were used. First, it was observed that 4E-BP1 was minimally phosphorylated in JAK2 wt Ba/F3 and Ba/F3-EPOR cells deprived of cytokines, while it was hyper-phosphorylated in V617F cells, supporting previous data on Akt constitutive activation in JAK2V617F-mutated cells. The addition of cytokines resulted in increased 4E-BP1 phosphorylation in JAK2 wt and V617F mutated Ba/F3 and Ba/F3-EPOR cells (data not shown). In cells incubated with RAD001, a marked inhibition of 4E-BP1 phosphorylation occurred (data not shown) and persisted up to at least 24 h (data not shown). STAT5 phosphorylation was greater in V617F cells compared to IL-3- or EPO-deprived JAK2 wt Ba/F3 or Ba/F3-EPOR cells, and it did increase substantially after cytokine exposure. STAT5 phosphorylation was significantly downregulated mirroring the effects on 4EBP1; inhibition was already evident at 60 min was maintained up to 24 h (not shown).

To confirm that attenuation of STAT5 phosphorylation was actually mediated by mTOR inhibition rather than resulting from a direct effect of RAD001 on STAT5 phopshorylation, mTOR was silenced with specific siRNA in HEL cells. Although siRNAs treatment decreased mTOR levels by only 50-60% at 24 h, the level of phosphorylated 4E-BP1 decreased dramatically compared to cells that had been treated with irrelevant control siRNA; total 4E-BP1 protein content did not change at all (data not shown). At 48 h, both mTOR and phosphorylated 4E-BP1 were barely detectable. At the same time, the level of phosphorylated STAT5 appeared markedly reduced at 24-48 h in cells that had been nucleofected with mTOR specific siRNA compared to control; total STAT5 concent did not change.

FIG. 2 shows the effect of selected mTOR inhibitors, a JAK1/JAK2 inhibitor, histone deacethylase inhibitors and hydroxyurea on mTOR and JAK/STAT signaling in SET2 cells. SET2 cells were incubated for 24 h with increasing concentrations of the drugs, and the level of total and phosphorylated JAK2, STAT5, and 4EBP1 was analyzed by western blot. Tubulin was used for loading normalization. The results shown are representative of two to four similar experiments for the different drugs.

Combination of RAD001 or PP242 with Compound A Results in Synergistic Inhibition of JAK2V617F Leukemic Cell Line Proliferation and Colony Formation The effects of concurrent inhibition of mTOR and JAK1/JAK2 in SET2 and V617F Ba/F3-EPOR cells were evaluated by measuring the proliferation inhibitory effects. Cells were incubated with different concentrations of RAD001 or PP242 and; by using these drug combinations a combination index (CI) ranging from 0.12 to 0.44 was measured suggesting strong synergistic activity of the two drugs (Table 3).

Further experiments using SET2 and Ba/F3 epoR V617F cells were performed in a clonogenic agar assay (Table 5); a CI ranging from 0.22 to 0.81 was measured in these cultures, again pointing to drug synergisms.

Combination of RAD001 or PP242 with Compound A Results in Synergistic Inhibition of Hematopoietic Progenitor Cells from Patients with MPN in EEC Colony Formation Assay.

To determine whether the proliferation of leukemic cells from MPN patients could be affected by simultaneous targeting of the mTOR and JAK pathway, PBMC from patients with PV were incubated with increasing concentration of RAD001, PP242, Compound A or a combination of RAD001 or PP242 and Compound A in an EEC assay. Peripheral-blood derived mononuclear cells from PV patients were cultured in EPO-free methylcellulose medium for EEC growth, in the absence or the presence of a fixed amount of RAD001, PP242, and/or Compound A. The EEC were scored at 12 day and expressed as percent of the number of colonies measured in control plates containing vehicle only. *, P<0.05, **, P<0.01. The results set forth in Table 6 show CIs of 0.2 and 0.26 in these cultures, further demonstrating synergism between mTOR and JAK inhibitors in the inhibition of JAK2V617F cell growth.

DISCUSSION

The MPN-associated JAK2V617F mutation determines a constitutive activation of the JAK2/STAT pathway; JAK2 inhibitors reduce the proliferation of JAK2V617F mutant cells in vitro, mitigate myeloproliferation in JAK2V617F transgenic animals (Liu P C, Caulder E, Li J, et al. Combined inhibition of Janus kinase 1/2 for the treatment of JAK2V617F-driven neoplasms: selective effects on mutant cells and improvements in measures of disease severity. Clin Cancer Res. 2009; 15:6891-6900) and produce measurable clinical improvement in patients with myelofibrosis (Verstovsek S, Kantarjian H, Mesa R A, et al. Safety and efficacy of INCB018424, a JAK1 and JAK2 inhibitor, in myelofibrosis. N Engl J. Med. 2010; 363:1117-1127) or hydroxyurea-resistant PV or ET. However, variations in JAK2V617F burden were modest and no molecular remission has been reported yet. Furthermore, the disease-initiating cell population in JAK2V617F knock-in mice was not affected by treatment with the JAK2 inhibitor TG101348. Overall, these observations present the possibility that effective targeting of MPN clone may not be achievable with available JAK2 inhibitors. Therefore, a more detailed knowledge of cellular signals involved in the dysregulated proliferation of mutant cells is desirable in order to design more effective therapeutic strategies. At this regard, it has been shown that co-treatment of the HDACi panobinostat and the JAK2 inhibitor TG101209 determined greater attenuation of JAK/STAT signaling in human and murine JAK2V617F-mutated cells and increased cytotoxicity against MPN CD34$^+$ cells compared to individual drugs.

This study focused on the mammalian target of rapamycin (mTOR), a key downstream target of the PI3k/Akt pathway. The serine/threonine kinase mTOR functions as a central regulator of cell metabolism, survival, growth, proliferation and autophagy. mTOR is inhibited by a family of molecules, named rapalogs following its founding member rapamycin, that have been recently employed in clinical trials in cancers. mTOR exists in two complexes, TORC1 and TORC2. TORC1, formed with raptor, controls the level of cap-dependent mRNA translation and phosphorylates effectors such as the eukaryotic initiation factor 4E-binding protein 1 (4E-BP1) and S6 kinase 1 (S6K1). On turn, phosphorylated 4E-BP1 leads to inhibited binding to eukaryotic initiation factor 4E (eIF4E) and prevents translation activation of several genes, including cyclin D1, Bcl-2, Bcl-$X_L$, and vascular endothelial growth factor. On the other hand, S6K1 regulates cell growth by phosphorylating key targets such as eIFe4, mTOR, eukaryotic initiation factor 4B and elongation-2 kinase. Both eIF4E and SK1 have been involved in cellular transformation and are overexpressed in some poor-prognosis cancers. Additional components of TORC1 include mammalian LST8/G-protein β-subunit like protein (mLST8/GβL) and the recently identified partners PRAS40 and DEPTOR. mTOR also combines with Rictor in mTORC2, that is largely rapamicin insensitive, and is composed of GβL and mammalian stress-activated protein kinase interacting protein 1 (mSIN1); TORC 2 is involved in the phosphorylation of Akt at Ser473. This negative feedback loop from mTORC2 to Akt may, in some instances, result in exacerbated tumor progression, although RAD001 was reported to potently inhibited Akt activity in leukemic cells via suppression of both mTORC1 and mTORC2. To overcome possible limitations and drawbacks of allosteric mTOR inhibitors, such as RAD001, novel molecules that act as competitive inhibitors of the mTOR ATP active site have been developed; one of these, PP242 strongly suppresses both TORC1 and TORC2-mediated activities and exerted potent cytotoxicity against leukemia cells. RAD001 and PP242 were used to explore in vitro the putative role mTOR as target for therapy in MPN.

It was first demonstrated that mTOR inhibitors prompted an arrest of cell proliferation of JAK2V617F mutated human and murine leukemia cell lines at drug concentrations significantly lower than control cells (Table 1). Conversely, RAD001 did not induce cell death while PP242 cause some cell apoptosis as highest concentrations; thus, in these experimental settings, mTOR inhibitors are mainly cytostatic. This mode of action differed from the JAK1/JAK2 inhibitor Compound A and HDAC inhibitor panobinostat that all potently induced cell apoptosis (FIG. 1). On the other hand, it was demonstrated that cell proliferation inhibition caused by mTOR inhibitors was not affected by maximized activation of the JAK/STAT pathway that followed cytokine exposure of the Ba/FE and Ba/F3-EPOR cells, unlike the case for the JAK1/JAK2 inhibitor. The latter observation was on line with the demonstration that sensitivity to JAK2 inhibitors of erythroid progenitors from PV patients resulted suppressed by the addition of EPO to the culture medium, and indirectly suggests that mechanisms underlying cell proliferation inhibition by RAD001 are at least in part independent of cytokine-induced JAK/STAT activation. It was demonstrated that RAD001 was more selective against JAK2V617F mutated than wild-type progenitors in patients with PV since the number of V617F colonies decreased of a mean of 39% in favor of wild-type ones (Table 2).

A prevalent antiproliferative rather than pro-apoptotic effect of RAD001 has been demonstrated in several other cancer cells, and represents the rationale for combination therapy with agents that preferentially induce apoptosis. Bearing this in mind, the effects of combining mTOR and a JAK1/JAK2 inhibitor in vitro was explored and evidence of a significant synergism concerning the inhibition of proliferation (Table 3) clonogenic potential (Table 5) of leukemia cell lines was demonstrated. In addition, the formation of hematopoietic colonies by progenitor cells from MPN patients was synergistically inhibited by combining RAD001 or PP242 with the JAK1/JAK2 inhibitor Compound A (Table 6).

Analysis of key signalling molecules showed that RAD001 and PP242 inhibited the phosphorylation of the downstream target 4EBP1, while JAK1/JAK2 inhibitors and HDAC inhibitors reduced phosphorylation of both JAK2 and STAT; of note, HDAC inhibitors also reduced the expression of total JAK2 (FIG. 2). An intriguing observation was that mTOR inhibition due to RAD001 and PP242 was associated with an appreciable decrease of STAT5 phosphorylation, which was not accounted for by reduced total STAT5 protein content. This positive feedback between mTOR and STAT5 was substantiated by demonstrating a concurrent attenuation of 4E-BP1 and STAT5 phosphorylation with the use of specific inhibitory RNA (siRNA) against mTOR (data not shown). The degree of inhibition of STAT5 phosphorylation mediated by RAD001 was far less than with JAK1/JAK2 inhibitors that did not affect 4E-BP1 phosphorylation, suggesting that mTOR activation in MPN cells may be largely JAK2-independent. On the other hand, an HDAC inhibitor demonstrated a modest inhibition of phoshorylation of 4EBP1, although current data do not allow us to conclude whether this effect was direct or not. As a whole, these observations indicate that STAT5 phosphorylation can be affected by targeting JAK2- and mTOR-initiated signaling. In this regard, rapamycin-sensitive activation of STAT3 via receptor tyrosine kinase/PI3K/Akt signalling has been demonstrated in several cancer cells and mouse or human tumors.

TABLE 2

Effects of RAD001 on the proportion of JAK2 wild-type and V617F colonies in clonogenic assays of $CD34^+$ cells from MPN patients.

| | | JAK2 genotype | | |
|---|---|---|---|---|
| Pat. # | RAD001 (50 nM) | Wild-type (%) | V617F (%) | % decrease V617F |
| 1 | − | 80 | 20 | 70 |
| | + | 94 | 6 | |
| 2 | − | 53 | 47 | 15 |
| | + | 60 | 40 | |
| 3 | − | 28 | 72 | 21 |
| | + | 43 | 57 | |
| 4 | − | 52 | 48 | 17 |
| | + | 58 | 40 | |
| 5 | − | 68 | 32 | 72 |
| | + | 91 | 9 | |
| | | | Mean ± SD | 39 ± 29 |

TABLE 3

Combination of mTOR inhibitor and JAK1/JAK2 inhibitor results in synergistic activity in proliferation inhibition of SET2 cell line and JAK2V617F Ba/F3-EPOR cells.

| Cell line | $IC_{50}$(nM) | | Drug combination ($IC_{50}$, nM) | | CI index |
|---|---|---|---|---|---|
| SET2 | RAD001 | Compound A | RAD001 | Cmp A | |
| | 17,000 ± 3000 | 160 ± 24 | 3,0983 | 29 | 0.20 |
| | PP242 | Compound A | PP242 | Cmp A | |
| | 285 ± 11 | 160 ± 24 | 66 | 47 | 0.43 |

TABLE 1

Determination of $IC_{50}$ of mTOR inhibitors, a JAK1/JAK2 inhibitor, HDAC inhibitors and hydroxyurea using proliferation inhibition assay in human and murine JAK2V617F mutated and JAK2 wild-type control cell lines.

| | | | | BaF/3 − IL3 | | |
|---|---|---|---|---|---|---|
| DRUG | K562 | HEL | SET2 | WT | V617F | V617F + IL3 |
| RAD001 (nM) | 16,000 ± 2,500 | 14,000 ± 2,800 | 17,000 ± 3,000 ** | 2,600 ± 1,200 | 10 ± 4 ** | 10 ± 5 ** |
| PP242 (nM) | 8,300 ± 1000 | 1,500 ± 113 ** | 285 ± 11 ** | 3,400 ± 300 | 800 ± 200 ** | 1,600 ± 200 ** |
| Compound A (nM) | >20,000 | 790 ± 150 ** | 160 ± 24 ** | 1,600 ± 500 | 34 ± 2 ** | 1,700 ± 300 |
| Panobinostat (nM) | 31 ± 8 | 8 ± 3 * | 7 ± 2 * | N.D. | N.D. | N.D. |
| HuOH (µM) | 4,910 ± 15 | 410 ± 20 * | 330 ± 11 * | N.D. | N.D. | N.D. |

| | BaF/3 − EPOR | | |
|---|---|---|---|
| DRUG | WT | V617F | V617F + EPO |
| RAD001 (nM) | >10,000 | 651 ± 50 ** | 1,231 ± 100 ** |
| PP242 (nM) | 5,931 ± 1,000 | 500 ± 100 ** | 750 ± 100 ** |
| Compound A (nM) | 457 ± 15 | 220 ± 20 ** | 521 ± 45 |
| Panobinostat (nM) | N.D. | N.D. | N.D. |
| HuOH (µM) | N.D. | N.D. | N.D. |

* $P < 0.05$;
** $P < 0.00$.
N.D., not done

TABLE 3-continued

Combination of mTOR inhibitor and JAK1/JAK2 inhibitor results in synergistic activity in proliferation inhibition of SET2 cell line and JAK2V617F Ba/F3-EPOR cells.

| Cell line | IC$_{50}$(nM) | | Drug combination (IC$_{50}$, nM) | | CI index |
|---|---|---|---|---|---|
| JAK2V167F Ba/F3-EPOR | RAD001 | Compound A | RAD001 | Cmp A | |
| | 651 ± 50 | 220 ± 20 | 363 | 125 | 0.44 |
| | PP242 | Compound A | PP242 | Cmp A | |
| | 500 ± 100 | 220 ± 20 | 400 | 121 | 0.98 |

The IC$_{50}$ value was calculated in proliferation inhibition assay in the presence of different drug combinations. Reported is the median IC$_{50}$ value from at least 3 experiments of the drugs used in combination. The Combination Index (CI) was calculated according to Chou and Talaly as described in Materials and Methods. A CI < 1 indicates that the interaction of the two drugs is synergistic. The first two columns report, for convenience, the IC$_{50}$ value of the individual drugs as calculated from data in Table 1.

TABLE 4

Determination of IC$_{50}$ of RAD001, PP242 and INC242 using clonogenic assay for human and murine JAK2V617F mutated cell lines and controls.

| Cell line | IC$_{50}$ (nM) | | |
|---|---|---|---|
| | RAD001 | PP242 | Cmp A |
| K562 | 10,000 ± 3,500 | 3,800 ± 200 | >15,000 |
| HEL | 85 ± 30** | 172 ± 59** | 374 ± 177** |
| SET2 | 130 ± 30** | 62 ± 19** | 27 ± 9** |
| Ba/F3 JAK2 wild-type | 120 ± 13 | 100 ± 10 | 380 ± 120 |
| Ba/F3 JAK2 V167F | 6 ± 2** | 18 ± 7** | 15 ± 10** |
| Ba/F3 epoR JAK2 wild-type | 22 ± 10 | 308 ± 100 | 740 ± 100 |
| Ba/F3 epoR JAK2 V167F | 4 ± 2** | 47 ± 12** | 20 ± 15** |

The IC$_{50}$ value (i.e., the concentration of drug that reduced colony number to 50% that measured in control dishes with vehicle only) was calculated in agar clonogenic assay by enumerating the colonies on day 7 in the presence of different drug concentrations. In case of human cell lines, the control cell line was K562, while in case of murine cells the reference were Ba/F3 wild-type cells maintained in the presence of IL-3.
**P < 0.01.

TABLE 5

Combination of RAD001 or PP242 and INC242 results in synergistic activity in inhibition of clonogenic potential of human and murine JAK2V617F mutated cell lines.
IC$_{50}$ (nM)

| Cell line | | | Drug combination | | CI index |
|---|---|---|---|---|---|
| | RAD001 | Cmp A | RAD001 | Cmp A | |
| SET2 | 44 ± 15 | 27 ± 9 | 7 | 4 | 0.22 |
| | PP242 | Cmp A | PP242 | Cmp A | |
| | 62 ± 19 | 27 ± 9 | 17 | 7.6 | 0.81 |

TABLE 5-continued

Combination of RAD001 or PP242 and INC242 results in synergistic activity in inhibition of clonogenic potential of human and murine JAK2V617F mutated cell lines.
IC$_{50}$ (nM)

| Ba/F3 epoR JAK2 V617F | RAD001 | Cmp A | RA0001 | Cmp A | CI index |
|---|---|---|---|---|---|
| | 4 ± 2 | 20 ± 15 | 1.1 (1.3-1) | 5.9 (6.8-5.1) | 0.59 (0.85-0.34) |
| | PP242 | Cmp A | PP242 | Cmp A | |
| | 47 ± 12 | 20 ± 15 | 6.3 (10-2.5) | 2.7 (4.4-1.1) | 0.24 (0.38-0.1) |

The IC$_{50}$ value was calculated in clonogenic assay in agar by enumerating the colonies grown on day 7 of culture established in the presence of different drug combinations. Reported is the median value from at least 3 experiments of IC$_{50}$ of the two drugs used in combination. The Combination Index (CI) was calculated as described in Materials and Methods. A a CI < 1 indicates that the interaction of the two drugs is synergistic. The first two columns indicate the IC$_{50}$ value calculated for the individual drugs and are reported here from Table 4 for convenience.

TABLE 6

Combination of RAD001 or PP242 and INC242 results in synergistic activity in inhibition of clonogenic potential of human Peripheral Blood mononuclear cells from PV patients.
IC$_{50}$ (nM)

| Cells | | | Drug combination | | CI index |
|---|---|---|---|---|---|
| | RAD001 | Cmp A | RAD001 | Cmp A | |
| PBMC form PV patients | 15 ± 10 | 1.8 ± 1 | 1.9 | 0.2 | 0.26 |
| | PP242 | Cmp A | PP242 | Cmp A | |
| | 1 ± 0.7 | 1.8 ± 1 | 0.05 | 0.1 | 0.2 |

The IC$_{50}$ value was calculated in clonogenic assay in agar by enumerating the colonies grown on day 7 of culture established in the presence of different drug combinations. The Combination Index (CI) was calculated as described in Materials and Methods. A a CI < 1 indicates that the interaction of the two drugs is synergistic.

The invention claimed is:

1. A method of treating a myeloproliferative neoplasm in a subject in need thereof, comprising administering to the subject synergistically effective amounts of an mTOR inhibitor and (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, wherein the mTOR inhibitor is everolimus or 2-(4-Amino-1-isopropyl-1H-pyrazolo[3,4-d]pyrimidin-3-yl)-1H-indol-5-ol.

2. The method of claim 1, wherein the mTOR inhibitor is everolimus.

3. The method of claim 1, wherein the mTOR inhibitor and (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, are in a single formulation or unit dosage form.

4. The method of claim 3, further comprising a pharmaceutically acceptable carrier.

5. The method of claim 1, wherein the mTOR inhibitor and (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, are administered separately.

6. The method of claim 1, wherein the myeloproliferative neoplasm is selected from the group consisting of chronic myeloid leukemia (CML), polycythemia vera (PV), essential thrombocythemia (ET), primary or idiopathic myelofibrosis (PMF), chronic neutrophilic leukemia, chronic eosinophilic leukemia, chronic myelomonocytic leukemia, juvenile myelomonocytic leukemia, hypereosinophilic syndrome, systemic mastocytosis, and atypical chronic myelogenous leukemia.

7. The method of claim 1, wherein the myeloproliferative neoplasm is primary myelofibrosis, post-polycythemia vera myelofibrosis or post-essential thrombocythemia myelofibrosis.

8. The method of claim 5, wherein the subject is human.

9. The method of claim 5, wherein the treatment comprises administering the mTOR inhibitor and (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, at substantially the same time.

10. The method of claim 5, wherein the treatment comprises administering the mTOR inhibitor and (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, at different times.

11. The method of claim 10, wherein the mTOR inhibitor is administered to the subject, followed by administration of (3R)-3-cyclopentyl-3-[4-(7H-pyrrolo[2,3-d]pyrimidin-4-yl)-1H-pyrazol-1-yl]propanenitrile, or a pharmaceutically acceptable salt thereof.

12. The method of claim 10, wherein (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, is administered to the subject, followed by administration of the mTOR inhibitor.

13. The method of claim 5, wherein the mTOR inhibitor and (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, are in separate formulations or unit dosage forms.

14. The method of claim 5, wherein the mTOR inhibitor and/or (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, are administered at dosages that would not be effective when one or both of the mTOR inhibitor and (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, are administered alone, but which amounts are effective in combination.

15. A method of inhibiting STAT5 phosphorylation, comprising administering synergistically effective amounts of an mTOR inhibitor and (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, wherein the mTOR inhibitor is everolimus or 2-(4-Amino-1-isopropyl-1H-pyrazolo[3,4-d]pyrimidin-3-yl)-1H-indol-5-ol.

16. The method of claim 15, wherein the mTOR inhibitor and (3R)-3-cyclopentyl-3-[4-(7H-pyrrolo[2,3-d]pyrimidin-4-yl)-1H-pyrazol-1-yl]propanenitrile, or a pharmaceutically acceptable salt thereof are administered to a subject in need thereof.

17. The method of claim 16, wherein the administration of the mTOR inhibitor and (3R)-3-cyclopentyl-3-[4-(7H-pyrrolo[2,3-d]pyrimidin-4-yl)-1H-pyrazol-1-yl]propanenitrile, or a pharmaceutically acceptable salt thereof treats a myeloproliferative neoplasm in the subject.

18. The method of claim 17, wherein the myeloproliferative neoplasm is selected from the group consisting of chronic myeloid leukemia (CML), polycythemia vera (PV), essential thrombocythemia (ET), primary or idiopathic myelofibrosis (PMF), chronic neutrophilic leukemia, chronic eosinophilic leukemia, chronic myelomonocytic leukemia, juvenile myelomonocytic leukemia, hypereosinophilic syndrome, systemic mastocytosis, and atypical chronic myelogenous leukemia.

19. The method of claim 17, wherein the myeloproliferative neoplasm is primary myelofibrosis, post-polycythemia vera myelofibrosis or post-essential thrombocythemia myelofibrosis.

20. A composition comprising an mTOR inhibitor and (3R)-3-cyclopentyl-3-[4-(7H-pyrrolo[2,3-d]pyrimidin-4-yl)-1H-pyrazol-1-yl]propanenitrile, or a pharmaceutically acceptable salt thereof in synergistically effective amounts, wherein the mTOR inhibitor is everolimus or 2-(4-Amino-1-isopropyl-1H-pyrazolo[3,4-d]pyrimidin-3-yl)-1H-indol-5-ol.

21. The composition of claim 20, further comprising a pharmaceutically acceptable carrier.

22. A method of treating a myeloproliferative neoplasm in a subject in need thereof, comprising administering to the subject an effective amount of the composition of claim 20.

23. A method of treating a myeloproliferative neoplasm in a subject in need thereof, comprising administering to the subject synergistically effective amounts of an mTOR inhibitor and (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, wherein the mTOR inhibitor is everolimus.

\* \* \* \* \*